US007807368B2

(12) United States Patent
Zagon et al.

(10) Patent No.: US 7,807,368 B2
(45) Date of Patent: Oct. 5, 2010

(54) CYCLIN-DEPENDENT KINASE INHIBITORS AS TARGETS FOR OPIOD GROWTH FACTOR TREATMENT

(76) Inventors: Ian S. Zagon, 589 Cook Ct., Hummelstown, PA (US) 17036; Patricia J. McLaughlin, 5535 Partridge Ct., Harrisburg, PA (US) 17111; Michael F. Verderame, 1882 Sand Hill Rd., Hershey, PA (US) 17033

( * ) Notice: Subject to any disclaimer, the term of this patent is extended or adjusted under 35 U.S.C. 154(b) by 263 days.

(21) Appl. No.: 11/901,770

(22) Filed: Sep. 19, 2007

(65) Prior Publication Data

US 2008/0146512 A1 Jun. 19, 2008

Related U.S. Application Data

(60) Provisional application No. 60/845,644, filed on Sep. 19, 2006.

(51) Int. Cl.
*C12Q 1/68* (2006.01)

(52) U.S. Cl. .......................... 435/6; 435/7.1; 435/7.23; 514/2

(58) Field of Classification Search ...................... None
See application file for complete search history.

(56) References Cited

U.S. PATENT DOCUMENTS 4,537,878 A * 8/1985 Plotnikoff ..................... 514/2

OTHER PUBLICATIONS

Zagon et al., Cancer Letters, Jan. 30, 1997;112(2):167-75.*
McLaughlin et al., Cancer Letters (2003) vol. 199, pp. 209-217.*
Abbruzzese, J (2002) Cancer, vol. 95, pp. 941-945.*
Cheng F. et al., "The Opioid Growth Factor (OGF)—OGF Receptor Axis Uses the p16 Pathway to Inhibit Head and Neck Cancer", *Cancer Research* 67(21):10511-10518 (2007).
Cheng F. et al., "The OGF-OGFr Axis Utilizes the p21 Pathway to Restrict Progression of Human Pancreatic Cancer", *Molecular Cancer* 7(5):1-12 (2008).
Donahue R.N. et al., "Cell Proliferation of Human Ovarian Cancer is Regulated by the Opioid Growth Factor-Opioid Growth Factor Receptor Axis", *Am J Physiol Regul Integr Comp Physiol 296*:R1716-R1725 (2009).
Cheng F. et al., "The OGF-OGFr Axis Utilizes the $p16^{INK4a}$ and $p21^{WAF1/CIP1}$ Pathways to Restrict Normal Cell Proliferation", *Molecular Biology of the Cell* 20:319-327 (2009).
Zagon I.S. et al., "The Biology of the Opioid Growth Factor Receptor (OGFr)", *Brain Research Reviews* 38:351-376 (2002).

* cited by examiner

*Primary Examiner*—Misook Yu
(74) *Attorney, Agent, or Firm*—Scully, Scott, Murphy & Presser, P.C.

(57) ABSTRACT

The present invention provides methods of cell cycle control by administering opioid growth factor (OGF), which activates opioid growth factor receptor (OGFr) signaling. Particularly, the present invention provides a method for monitoring OGF modulation or treatment of a cell proliferation or growth related condition in a subject by assessing the level of the cyclin dependent kinase inhibitor (CKI) relevant or corresponding to the condition. The present invention also provides a method for screening the eligibility of a subject for OGF modulation or treatment by assessing the level of OGF receptor (OGFr) and the relevant CKI. A method for enhancing the efficacy of OGF therapy by increasing the level of the relevant CKI and/or OGFr is also provided.

19 Claims, 10 Drawing Sheets

CYCLIN-DEPENDENT KINASE INHIBITORS AS TARGETS FOR OPIOD GROWTH FACTOR TREATMENT

CROSS REFERENCE TO RELATED APPLICATIONS

This application claims priority of U.S. Provisional Application No. 60/845,644, filed Sep. 19, 2006.

FIELD OF THE PRESENT INVENTION

The present invention relates generally to the field of modulating cell proliferation. Specifically, the present invention relates to diagnostics and therapeutics of cell growth or proliferation related disorders. More specifically, the invention relates to monitoring and enhancing opioid growth factor (OGF) modulation and therapy. The present invention also relates to enhancing normal cell proliferation, e.g., in burn patients.

BACKGROUND OF THE PRESENT INVENTION

Various publications, including patents, published patent applications, technical or scholarly literatures and articles are cited throughout the present application. Each of these cited publications is incorporated by reference herein, in its entirety and for all purposes.

Opioid growth factor (OGF) is an endogenous opioid peptide ([$Met^5$]-enkephalin) which belongs to a class of endogenous opioid proteins believed to be important in the growth of normal and neoplastic cells, and in renewing and healing tissues, in prokaryotes and eukaryotes (Zagon, I. S. et al., In: Cytokines: Stress and Immunity. Plotnikoff N P et al., (eds). CRC Press, Boca Raton, Fla., pp. 245-260, 1999).

OGF is directly involved in growth processes, and serves as a negative regulator in a wide variety of cells and tissues (Zagon, I. S. et al., In: Receptors in the Developing Nervous System. Vol. 1. Zagon, I. S. and McLaughlin, P. J. (eds). Chapman and Hall, London, pp. 39-62, 1993). OGF is known to modulate cell proliferation and tissue organization during development, cancer, cellular renewal, wound healing and angiogenesis (Zagon et al., Brain Res 1999; 849(1-2):147-154).

OGF action is mediated by specific and saturable binding to a receptor called the OGF receptor or OGFr (Zagon et al., Brain Res Brain Res Rev. 2002 February; 38(3):351-76). OGFr has been cloned and sequenced in human, rat, and mouse and is characterized by containing a series of imperfect sequence repeats. Although the OGF receptor resembles classical opioid receptors pharmacologically, the OGF receptor has no resemblance to classical opioid receptors either at the nucleotide or protein levels. OGFr is associated with the outer nuclear envelope. The peptide-receptor complex associates with karyopherin, translocates through the nuclear pore, and can be observed in the inner nuclear matrix and at the periphery of heterochromatin of the nucleus, where OGF-OGFr signaling is thought to modulate DNA activity.

The interaction of OGF with OGFr to regulate cell replication serves as an active negative growth factor in neoplasia. As previously shown by Zagon et al. (Int. J. Oncology 17:1053-1061 (2000)), OGF acts on cell proliferation by targeting the G0/G1 phase of the cell cycle. OGF treatment resulted in a protraction of the G0/G1 phase, and therefore fewer cells enter mitosis and divide, resulting in the net effect of slowing growth progression.

The transition from one cell cycle phase to another is tightly regulated by different proteins that act at cell cycle control checkpoints. Key regulator proteins are the cyclin-dependent kinases (CDK), a family of serine/threonine kinases that are activated at specific points of the cell cycle. Thus far, there have been nine CDKs identified and, of these, five are active during the cell cycle. During G1 phase, CDK4, CDK6 and CDK2 are active. During S phase, CDK2 is active. During G2 and M phase, CDK1 is active.

CDK protein levels remain stable during the cell cycle, in contrast to their activating proteins, the cyclins. Cyclin protein levels rise and fall during the cell cycle and in this way they periodically activate CDK. Different cyclins are required at different phases of the cell cycle. The three D type cyclins (cyclin D1, cyclin D2 and cyclin D3) bind to CDK4 and CDK6 and CDK-cyclin D complexes are essential for entry into G1. Another G1 cyclin is cyclin E, which associates with CDK2 to regulate progression from G1 into S phase. Cyclin A binds with CDK2 and this complex is required during S phase. In G2 and early M phase, cyclin A complexes with CDK1 to promote entry into M. Mitosis is further regulated by cyclin B in complex with CDK1.

When activated, CDKs induce downstream processes by phosphorylating selected proteins. The most frequently studied target is the substrate of CDK4/6-cyclin D, i.e., the retinoblastoma (Rb) protein. During early G1, Rb becomes phosphorylated and this leads to disruption of a complex with various transcription factors, in particular, those belonging to the E2F family, which positively regulate the transcription of genes whose products are required for S phase progression (Nevins et al., Hum Mol Genet 10:699-703 (2001)).

Rb is one of the best characterized tumor suppressors and is recognized to participate in the regulation of the cell cycle, senescence, developmental processes, tissue homeostasis, and responses to chemotherapy. Its inactivation in almost every cancer and its intricate mode of operation and regulation has been widely reported (Liu et al., Curr Opin Genet Dev 14:55-64 (2004); Fan et al., Apoptosis 4:21-29 (1999)).

Rb belongs to a family of proteins known as "pocket proteins" (PP) which include Rb, p107 and p130 (Tonini et al., J Cell Physiol 192:138-150 (2002). Although all three protein are inactivated in various cancer cells, Rb emerged as the most pertinent tumor suppressor.

Rb suppressive activity is modulated by external stimuli that trigger the intracellular cascade of events that influence Rb interaction with E2F transcription factors. Hypo-phosphorylated Rb binds to E2F and suppresses E2F-dependent gene transcription. Phosphorylation releases Rb from E2F-bound promoters during the G1 (resting) phase of the cell cycle, leading to the accumulation of transcriptionally active E2F and activation of genes required for progression into the S-phase. Thus, the Rb phosophorylation state correlates with the well-characterized G1-S cell cycle restriction point.

Rb phosphorylation levels, in turn, are controlled by CDK kinases and CDK kinase inhibitors. CDK activity is governed, in part, by association with cell cycle inhibitory proteins called CDK inhibitors (CKI) which bind to CDK alone or to the CDK-cyclin complex and regulate CDK activity. Two distinct families of CKIs have been discovered, the INK4 family and Cip/Kip family, based on activity and sequence homology. The INK4 family includes p15 (INK4b), p16 (INK4a), p18 (INK4c), p19 (INK4d), which specifically inactivate G1 CDKs, i.e., CDK4 and CDK6. These CKI form stable complexes with the CDK enzyme before cyclin binding, preventing association with cyclin D. Inactivation of p16 is common in cancer in general and melanoma genesis in particular. The second family of inhibitors, the Cip/Kip family, includes p21 (Waf1, Cip1), p27 (Cip2), p57 (Kip2). These inhibitors inactivate G1 CDK-cyclin complexes (cyclin D-CDK4, cyclin D-CDK6 and cyclin E-CDK2) and to a lesser extent, CDK1-cyclin B complexes. Although p21 and p27 inhibit all CDK4/6 and CDK2 activity at high concentration, further analysis revealed that at physiological concentrations, cyclin E-CDK2 activity is inhibited whereas complex formation between CDK4/6 and cyclin D is augmented by p21 and p27, enhancing their kinase activity. This observation is in agreement with studies in which inactivating mutations in p16 facilitates immortalization of human melanocytes in culture but does not alter growth factor requirement. Likewise, mouse melanocytes with targeted disruptions in the p16, p21 or p27 became immortalized as their wild type counterparts and did not lose their dependency on external growth factor. However, disruption of p21 or p27, but not p16, accelerated melanocyte death in growth factor-deprived medium, suggesting that their presence protects the cells from apoptosis.

The underlying signaling mechanism by which OGF acts to negatively regulate cellular proliferation has been poorly understood. Currently, OGF is being used effectively as a chemotherapeutic agent, either alone or in combination with standard chemotherapies to treat a variety of cancers, including squamous cell carcinoma of the head and neck (SCCHN) and pancreatic adenocarcinoma. Although it is known that OGF acts on cell proliferation by targeting the G0/G1 phase of the cell cycle, the downstream effect or pathways that are involved have not been elucidated. Due to the critical role that the CDKs play in regulating cell cycle, a better understanding of the relationship between OGF and the CDK pathway is needed.

Therefore, there remains a need for a better understanding of the underlying mechanism of OGF's action and its relationship with the CDK pathway in regulating cell cycle. This understanding will provide improvements to the current methods of treating various types of cancers using OGF by enhancing the efficacy and responsiveness of current OGF therapy.

OGF is a tonic inhibitory peptide that modulates cell proliferation and migration, as well as tissue organization, during development, cancer, homeostatic cellular renewal, wound healing, and angiogenesis. Its' action is mediated by the OGFr.

Previous studies have demonstrated the effectiveness of OGF as a useful agent in inhibiting tumor growth in a number of different tissues. Recent studies are directed at comparing the effectiveness of using either OGF alone or in combination with other chemotherapeutic agents in inhibiting tumor growth.

A major question in the use of OGF treatment or therapy has been identifying the eligibility of individuals who will be responsive to therapy with this agent. Moreover, the effectiveness of OGF therapy may be enhanced if other modalities were used in conjunction with this agent. A solution to these problems lies in understanding the underlying pathway of the OGF-OGFr axis in terms of influencing cell proliferation.

SUMMARY OF THE PRESENT INVENTION

The invention recognizes that opioid growth factor (OGF) treatment results in decreased level of retinoblastoma (Rb) protein phosphorylation, or, alternatively, with increased expression of a cyclin-dependent kinase (CDK) inhibitor (CKI) in a cell. The present invention provides methods of cell cycle control by administering opioid growth factor (OGF) which activates opioid growth factor receptor (OGFr) signaling.

In certain aspects of the present invention, the cell is an animal cell in vitro or ex vivo. In other aspects, the cell is an animal cell in vivo. In certain preferred aspects, the animal cell is a human cell. In some aspects, the CDK inhibitor includes, but is not limited to, p15, p16, p18, p19, p21, p27 and p57, preferably, p16 or p21. In some aspects, the opioid growth factor is administered to the animal at a dose of from about 20 to 1000 μg/kg body weight, preferably from about 100 to 400 μg/kg body weight. In some aspects, the cell is a neoplastic cell.

In one aspect, the present invention is directed to a method for monitoring the sensitivity of opioid growth factor (OGF) modulation or treatment of a cell proliferation or growth related condition in a subject, comprising assessing the level of the cyclin dependent kinase inhibitor (CKI) relevant or corresponding to the condition or the level of the CKI/cyclin dependent kinase (CDK) complex in the subject. In a particular aspect of the present invention, the modulation or treatment of the condition results in increased cell growth or proliferation comprising decreasing, disrupting or inhibiting OGFr expression in the cell to be modulated or treated. The detection can be conducted by standard methods well established and known in the art, including, but not limited to, ELISA, radioimmunoassay, Western blotting techniques, or by DNA or RNA methodology including PCR, Northern blotting, or Southern blotting.

In another aspect, the present invention is directed to a method for screening the eligibility of a subject for opioid growth factor (OGF) modulation or treatment of a cell proliferation or growth related condition, comprising assessing the level of OGF receptor (OGFr) and the cyclin dependent kinase inhibitor (CKI) relevant or corresponding to the condition in the cell to be modulated or treated, wherein the cell having at least one molecule of OGFr and one molecule of the CKI indicates the subject's eligibility.

In still another aspect, the present invention is directed to a method for enhancing the efficacy of opioid growth factor (OGF) modulation or treatment of a cell growth or proliferation related disorder in a subject, comprising increasing the level of the cyclin dependent kinase inhibitor (CKI) relevant or corresponding to the disorder in the cell to be modulated or treated and administering to the subject an effective amount of OGF to the subject. In a particular aspect, the method further includes enhancing the expression of the OGF receptor (OGFr) in the cells to be modulated or treated.

In yet another aspect, the present invention is directed to a method for enhancing the efficacy of opioid growth factor (OGF) modulation or treatment of a cell growth or proliferation related disorder in a subject, comprising enhancing the expression of the OGF receptor (OGFr) in the cells to be modulated or treated, and administering to the subject an effective amount of OGF. In a particular aspect, the method further includes increasing the level of the cyclin dependent kinase inhibitor (CKI) relevant or corresponding to the disorder in the cells to be modulated or treated.

In still yet another aspect, the present invention is directed to a method for monitoring the sensitivity or efficacy of opioid growth factor (OGF) modulation or treatment of a cell growth or proliferation related disorder in a subject, comprising assessing level of retinoblastoma (Rb) protein phosphorylation in the subject.

A further aspect of the present invention provides a method for treating a non-cancerous disease related to aberrant cell growth and proliferation in a subject, comprising administering to the subject an effective amount of OGF, wherein the cell to be treated comprises at least one opioid growth factor receptor.

One aspect of the present invention also provides a method for delaying the onset of tumorigenesis in an animal cell containing an opioid growth factor receptor. The method comprises the step of administering to the cell OGF in combination with at least one relevant CDK inhibitor. In certain preferred aspects, the relevant CDK inhibitor includes, but is not limited to, p15, p16, p18, p19, p21, p27 and p57.

Another aspect of the present invention also provides a method for slowing the progression of tumorigenesis in an animal cell comprising an opioid growth factor receptor. The method comprises the step of administering to the cell OGF in combination with at least one relevant CDK inhibitor. In certain preferred aspects, the relevant CDK inhibitor includes, but is not limited to, p15, p16, p18, p19, p21, p27 and p57.

Still another aspect of the present invention provides a method for treating a hyperproliferative disorder, the progression of tumorigenesis, an inflammatory disorder or an immune disorder, characterized by aberrant cell proliferation. The method comprises the step of administering to the cell OGF in combination with at least one relevant CDK inhibitor in an animal cell comprising an opioid growth factor receptor. In certain preferred aspects, the CDK inhibitor includes, but is not limited to, p15, p16, p18, p19, p21, p27 and p57.

DETAILED DESCRIPTION OF THE PRESENT INVENTION

Figure 1:
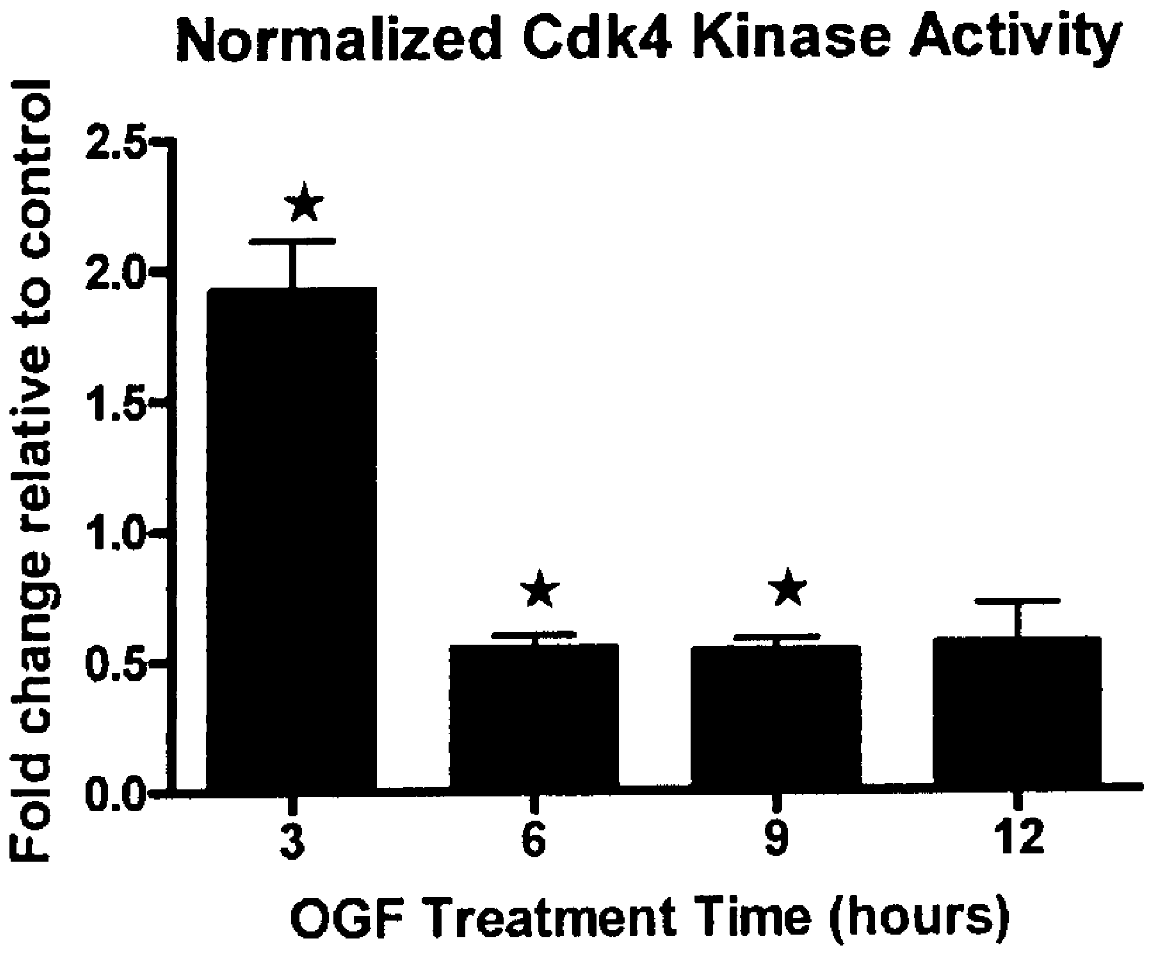
FIG. 1. Cdk4 kinase activity was evaluated in synchronized SCC-1 cells treated with OGF for 3, 6, 9, or 12 h. Cdk4 kinase activity was measured as the capacity of phosphorylation of Rb protein in the presence of radioactive ATP. Densitometric analysis of the Western blots was performed, and the Cdk4 activity was measured relative to controls. Values represent means±SE for 3 independent experiments. Kinase activity values from OGF-treated cultures differed significantly ($p<0.05$, *) from control cells at each respective time.

Studies have demonstrated the important role of opioid growth factor (OGF) in regulating cell cycle, with OGF action directed specifically to the $G_0/G_1$ phase of the cell cycle with the net effect of slowing growth. However, the underlying mechanism or the target of OGF's action has not been fully elucidated.

The present invention recognizes a link between the OGF treatment, OGFr signalling and cyclin-dependent kinase (CDK) pathways that, for example, regulate the cell cycle. Specifically, the present invention recognizes that activation of the OGF treatment inhibits cell replication by increasing the activity of various CDK inhibitors (CKI). An increase in the activity of CDK inhibitors, in turn, represses the activity of CDKs and their ability to phosphorylate their substrates, in particular, the retinoblastoma (Rb) protein. As a result, hypophosphorylated Rb binds to E2F and suppresses E2F-dependent gene transcription during the G1 phase of the cell cycle, with a net effect of inhibiting cell proliferation. Without intending to be bound by any particular mechanism, it is believed that other OGF effects are similarly mediated through CDK inhibitory pathways.

Accordingly, the present invention provides methods of cell cycle control by administering opioid growth factor (OGF), which activates opioid growth factor receptor (OGFr) signaling.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of, cell and tissue culture, cancer cell biology, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N.Y. (2000); and Kufe et al., Cancer Medicine, 6th ed., B.C. Decker Inc., Hamilton, Canada (2003). The nomenclatures used in connection with, and the laboratory procedures and techniques of, molecular and cellular biology and medicinal and pharmaceutical chemistry described herein are those well known and commonly used in the art. Standard techniques are used for chemical syntheses, chemical analyses, pharmaceutical preparation, formulation, and delivery, and treatment of patients. In case of conflict, the present specification, including definitions, will control. The materials, methods, and examples are illustrative only and not intended to be limiting.

Throughout this specification, the word "comprise" or variations such as "comprises" or "comprising" will be understood to imply the inclusion of a stated integer or groups of integers but not the exclusion of any other integer or group of integers.

As used herein, the term "opioid growth factor (OGF) or [$Met^5$]-enkephalin" refers to all modifications, substitutions, truncations, analogs or derivatives of OGF or [$Met^5$]-enkephalin which retain the ability to interact with and/or activate the OGF receptor (OGFr). This term is also meant to include natural or synthetic compounds that mimic the biological activity of OGF in its interaction with an OGF receptor, i.e., that trigger OGF receptor function.

By "OGF-OGFr axis" is meant that the pentapeptide OGF functions together with its receptor OGFr, i.e., both OGF and OGFr have to be present and functional in order to influence growth. The term also means the signal pathway related to OGF and OGFr interaction.

As used herein, the term "effective amount" of OGF refers to an amount of OGF sufficient to produce a desired effect. For example, an "effective amount" of OGF shall mean a concentration of OGF sufficient to decrease the level of Rb protein phosphorylation. Alternatively, an "effective amount" of OGF shall mean a concentration of OGF sufficient to increase the expression of a CDK inhibitor (CKI). The precise amount of OGF to be effective depends upon the condition of the cell that is being treated. When the cell is in vivo, it may depend on the weight of the subject, as well as the route of administration. As a general rule, for intravenous administration, regimes in cumulative amounts ranging from about 10 mg to about 30 mg (or about 25 μg/kg to about 300 μg/kg) exogenous OGF per day for a human patient is effective. For subcutaneous administration, regimes in cumulative amounts ranging from about 1 mg/ml to about 5 mg/ml (or about 10 μg/kg to about 50 μg/kg) of exogenous OGF per day are effective.

As used herein, the terms "cyclin dependent kinase" or "CDK" are art recognized terms referring to a protein of the family of proteins that includes catalytic subunits of cyclin/CDK complexes. Exemplary CDK proteins include CDK2, CDK2, CDK3, CDK4, CDK5, CDK6 and CDK7.

As used herein the terms "CDK Inhibitor" or "CKI" refers to a molecule able to decrease or prevent activation of a kinase activity of a cyclin dependent kinase (CDK) either by, for example, inhibiting formation of CDK complexes including regulatory subunits, inhibiting interaction of the CDK subunit with activating kinases or phosphatases, inhibiting substrate binding, inhibiting ATP binding, and/or inhibiting conformational changes required for enzymatic activity. Accordingly, such inhibition may be by a direct mechanism or by an indirect mechanism, including by competitive, non- or uncompetitive mechanisms. Exemplary CKI proteins include members of the INK4 family, such as includes p15 (INK4b), p16 (INK4a), p18 (INK4c) and p19 (INK4d), and members of the Cip/Kip family, such as p21 (Waf1, Cip1), p27 (Cip2) and p57 (Kip2). Other CKIs are inevitably going to be identified in the future and are intended to be encompassed by the present invention. The CDK inhibitor of the present invention includes, but is not limited to, p15, p16, p18, p19, p21, p27 and p57.

By "relevant CKI" or "corresponding CKI" is meant a CKI related to a condition or disease that is to be treated or modulated. For example, p16 is a relevant or corresponding CKI of squamous cell carcinoma of the head and neck (SCCHN) and similarly, p21 is a relevant or corresponding CKI of pancreatic cancer. According to the present invention, a condition or disease eligible for OGF treatment or therapy has at least one type of relevant or corresponding CKI.

By "modulate" or "modulating" or "modulation" is meant to adjust, alter or keep a level or condition to or in a proper measure or proportion. The term "modulate" or "modulating" or "modulation" as used herein includes the inhibition or suppression of a function or activity (such as cell proliferation) as well as the enhancement of a function or activity.

By "treatment" or therapy is meant an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" or "therapy" can also mean prolonging survival as compared to expected survival if not receiving treatment.

By "palliating" a disease or disorder means that the extent and/or undesirable clinical manifestations of a disorder or a disease state are lessened and/or time course of the progression is slowed or lengthened, as compared to not treating the disorder.

To "inhibit" or "suppress" or "reduce" a function or activity, such as cancer cell proliferation or a gene expression, is to reduce the function or activity when compared to otherwise same conditions except for a condition or parameter of interest, or alternatively, as compared to another conditions.

As used herein, the term "Rb" or "retinoblastoma protein" refers to the product of the retinoblastoma tumor suppressor gene. Rb is a nuclear phosphoprotein which acts as an inhibitor of cell proliferation.

As used herein, the term "tumorigenesis" refers to the abnormal uncontrolled growth or proliferation of cells, leading to the formation of tumors.

As used herein, the term "neoplastic cell" refers to any cell that displays undesired proliferation and/or growth. Neoplastic cells thus include but are not limited to cancer cells, e.g., may be hyperproliferative cells.

As used herein, the term "cell" or "animal cell" shall be interpreted to include any cell derived from an animal, including a mammal (e.g., a human). The term encompasses cells grown in vitro, ex vivo, and those in vivo, and includes progeny of any of the above.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleoside or nucleotide analogs, and, as applicable to the embodiment being described, single (sense or antisense) and double- or multi-stranded polynucleotides.

By "subject" is meant a mammalian organism, preferably a human or other primate species.

By "cancer" or "cancerous disorders/diseases" is meant a group of diseases in which cells are aggressive (grow and divide without respect to normal limits), invasive (invade and destroy adjacent tissues), and/or metastatic (spread to other locations in the body).

Figure 9:
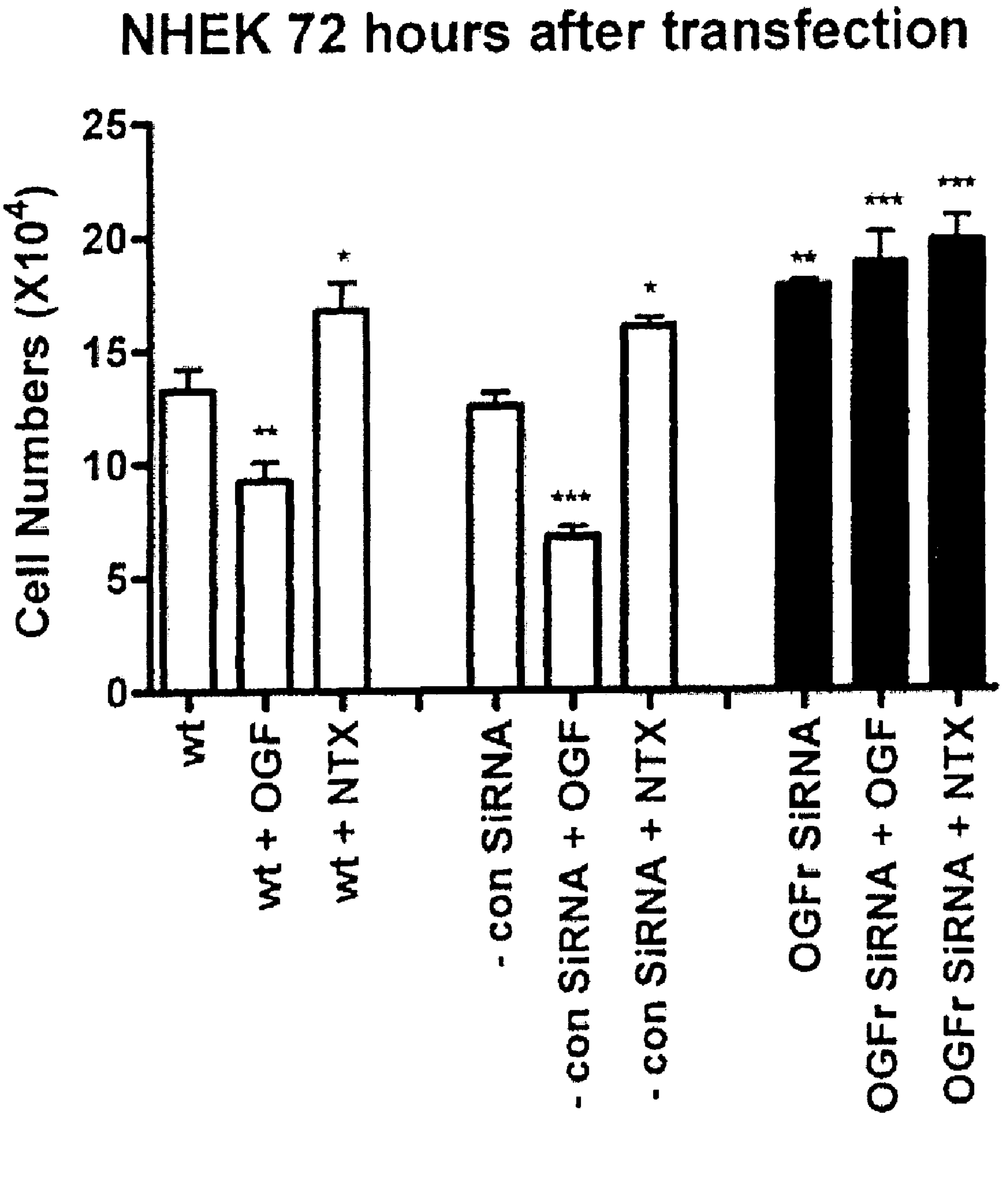
FIG. 9. OGFr is required for OGF action on growth. Normal Human Neo-Epidermal Keratinocyte cells (NHEK) were transfected with OGFr siRNAs or control siRNAs for 72 h in the presence of $10^{-6}$ M OGF, $10^{-6}$ M NTX, or sterile water. Cells were harvested at 72 h and counted with a hemacytometer. Data represent means±SE for 2 independent experiments. Cell numbers differed from wt cells or cells transfected with the negative control siRNA and treated with sterile water at $p<0.05$ (*), $p<0.01$ (), or $p<0.01$ (*).

By "cell proliferation or growth related condition" is meant a condition that is caused or controlled by abnormal cell cycle or is related to regulation of cell cycle or a condition in need of enhanced cell proliferation or growth. For example, cancer is a cell proliferation or growth related condition that is caused by aberrant cell division. In addition to cancer, other cell proliferation or growth related conditions or cell proliferative disorders involving aberrant or abnormal cell proliferation, which are also referred to as "non-cancerous disease related to aberrant cell growth or proliferation," include, but are not limited to, inflammatory diseases, allergies, autoimmune disease, graft rejection psoriasis, restenosis, artherosclerosis, and any other non-cancer disorder wherein it is desirable to inhibit, prevent or suppress cell growth. A cell proliferation or growth related condition referred to in the present application also include tissue injuries, such as skin injury caused by a burn, the treatment of which needs improved or enhanced cell growth or proliferation—by both in vivo or in tissue culture whereby cells can be transplanted after proliferation. By "burn" is meant any injury to mammalian skin caused by heat, cold, electricity, chemicals, friction or radiation (e.g. a sunburn). According to the present invention, a normal cell can be stimulated to be used for surgical procedures in a cell proliferation or growth related condition. See, e.g., Example 4 and FIG. 9.

In one embodiment, the present invention is directed to a method for monitoring the sensitivity of opioid growth factor (OGF) modulation or treatment of a cell proliferation or growth related condition in a subject, comprising assessing the level of the cyclin dependent kinase inhibitor (CKI) relevant or corresponding to the condition or the level of the CKI/cyclin dependent kinase (CDK) complex in the subject. According to the present invention, the sensitivity can be determined by assessing the subject's relevant CKI expression level before OGF administration (determining the baseline CKI expression level), administering an effective amount of OGF to the subject, assessing the subject's relevant CKI expression level after sufficient time upon the administration of OGF, and compare the subject's relevant CKI expression levels before (baseline) and after the administration of OGF, wherein the relevant CKI expression results in at least one relevant CKI molecule increase after the administration of OGF or at least one relevant CKI over the baseline level indicates that the subject is sensitive to OGF therapy. The sufficient time can be determined by one skilled in the art. For example, according to the present invention, the sufficient time can be few hours, one day, or one week after the administration of OGF. The monitoring or detection can use any tissue or cell, e.g., plasma, saliva, or other tissue/cells by DNA, RNA, or protein analysis (including, but not limited to, PCR, Northern blot, Western blot, ELISA, RIA).

According to the present invention, the target of OGF in a cell is CKI, such as p16 and p21. CDK4 kinase is known to bind to cyclin D and form CDK4-cyclin D complexes, which is essential during entry into G1 phase of the cell cycle. Example 2 describes that OGF-OGFr's influence on cell growth is mediated through the CDK inhibitor pathway, and in this particular cell line, by modulating the p16 protein. OGF treatment resulted in a significant induction of p16 protein expression in a receptor-mediated manner (see, e.g., FIGS. 2, 3).

Example 3 investigates the role of other CKIs in the regulation of the OGF-OGFr axis. Pancreatic cancer cell lines lacking p21 protein were examined. As illustrated in Example 3 and FIGS. 6 and 7, treatment of pancreatic tumor cells (e.g., BxPC3 and PANC-1 and Capan-2 cell lines) with OGF also resulted in significant reductions in Rb phosphorylation (see FIG. 5) and CDK2 kinase activity in connection with observed inhibition in cellular growth. CDK2 kinase is known to bind to cyclin E and form CDK2-cyclin E complexes which are essential to regulate progression from G1 to S phase. Example 3 illustrates that OGF-OGFr's influence on cell growth can also be mediated through another CDK inhibitor, the p21 protein, in pancreatic cancer cells. A significant induction of p21 protein expression in a receptor-mediated manner was observed in the BxPC3 cells following OGF treatment (see FIG. 7).

Figure 10:
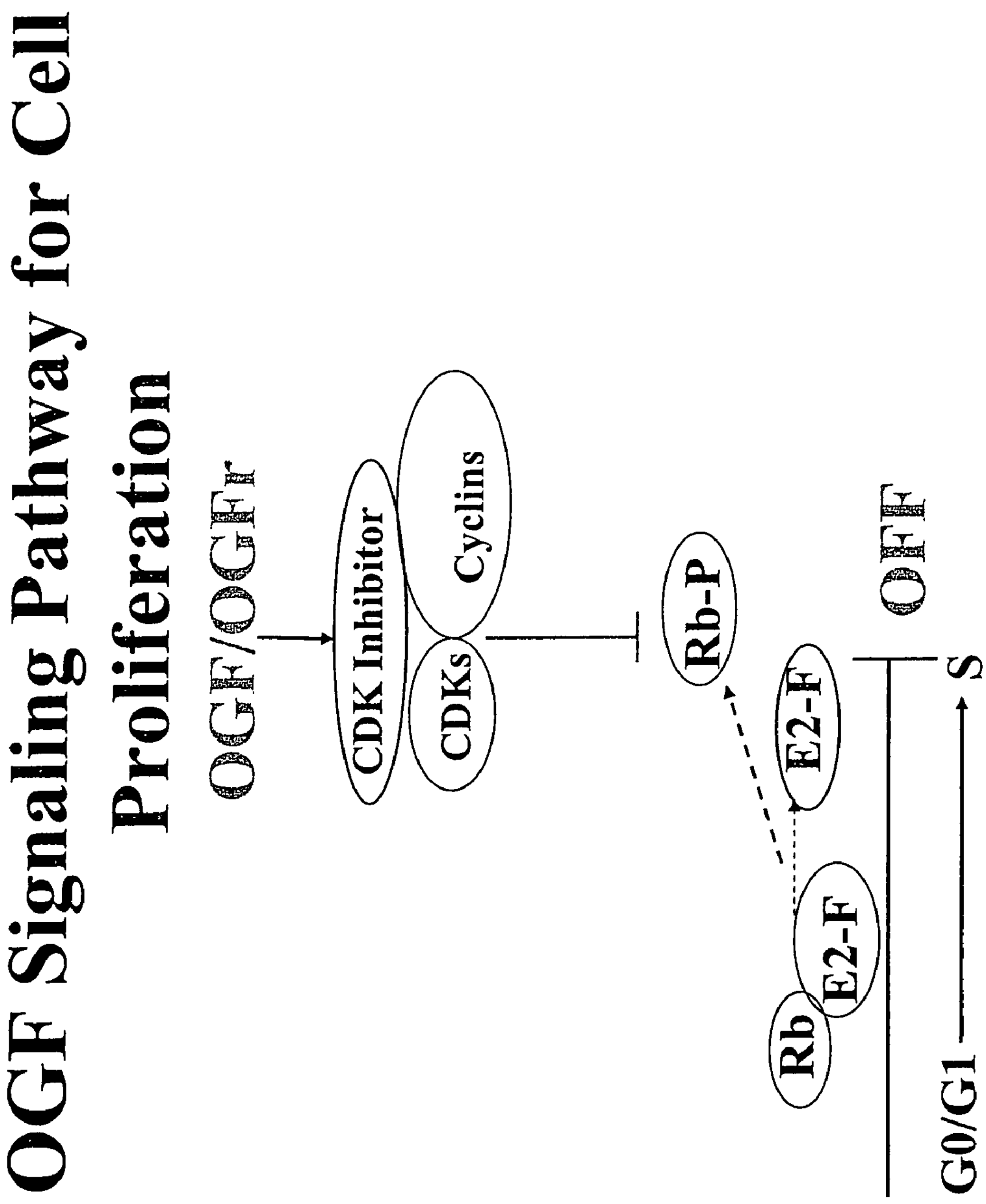
FIG. 10. Schematic pathway of the OGF-OGFr axis interaction and the cell cycle.

The present invention thus recognizes a connection between the OGF-OGFr axis and the progression of cells through $G_0/G_1$ to S phase of the cell cycle. As summarized in FIG. 10, without intending to be limited to any particular theory, it is believed that the effect of the OGF-OGFr axis is mediated by its regulation on CDKs, cyclins and CDK inhibitors, which in turn, collectively regulate Rb phosphorylation and cell cycle control.

For example, if the cell is one that expresses p16 and has OGFr, it will be identified as a cell that will be responsive to (i.e., whose cell growth and/or division will be delayed by) OGF therapy. One such exemplary cell is a squamous cell carcinoma cell, such as SCCHN. Similarly, if the cell is one that does not express p16 but does express p21 and has OGFr, it will be identified as a cell that will be responsive to OGF therapy. One such exemplary cell is a pancreatic carcinoma cell.

Accordingly, in one embodiment, the present invention also provides a method for inducing a relevant CKI, such as p16 or p21 protein, production in an animal cell containing an opioid growth factor receptor (OGFr) and the relevant CKI encoding nucleic acid sequences capable of expression, by administering an effective amount of OGF.

Figure 5:
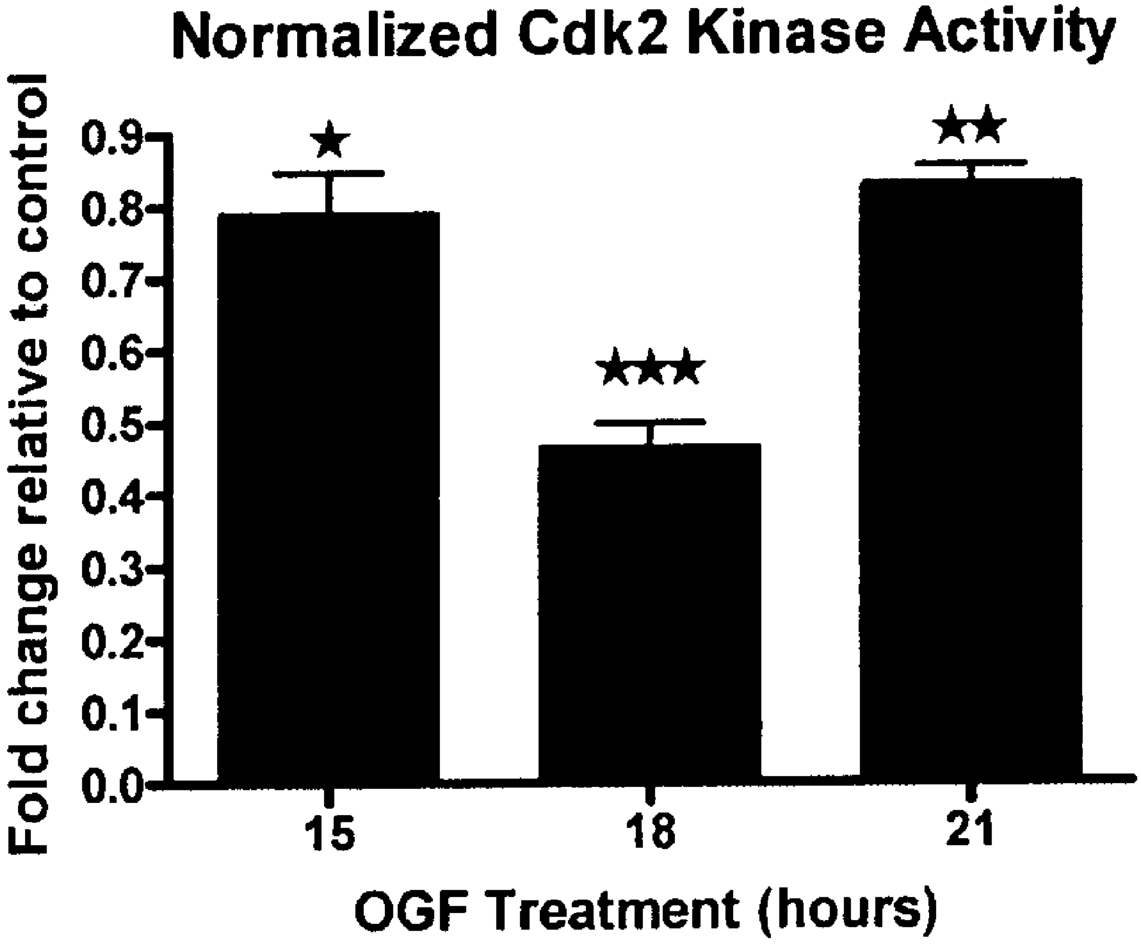
FIG. 5. Inhibition of Rb phosphorylation and Cdk2 kinase activity by OGF. Cdk2 kinase activity was evaluated in synchronized BxPC-3 cells treated with OGF for 15, 18 or 21 hours. Cdk2 kinase activity was measured as the capacity of phosphorylation of H1 protein in the presence of radioactive ATP. Densitometric analysis of the kinase assay was performed, and the Cdk2 activity was measured relative to controls. Values represent means±SE for 3 independent experiments. Kinase activity values from OGF-treated cultures were significantly reduced from control cells at each respective time point (*$p<0.05$, $p<0.01$, *$p<0.001$).

As illustrated in Examples 2 and 3, treatment with OGF of human squamous cell carcinoma of the head and neck cells (SCC-1) or pancreatic cells resulted in significant reductions in Rb phosphorylation and CDK4 or CDK2 kinase activity, although the Rb and CDK4 or CDK 2 protein levels remained relatively unchanged (see FIGS. 1, 5).

Accordingly, in another embodiment, the present invention also provides a method for decreasing the level of Rb protein phosphorylation in an animal cell containing an opioid growth factor receptor by administering an effective amount of OGF.

According to the present invention, in some particular embodiments, the cell is an animal cell in vitro or ex vivo. In other particular embodiments, the cell is an animal cell in vivo. In certain preferred embodiments, the animal cell is a human cell. In some embodiments, OGF is administered to a subject at a dose of from about 20 to about 1000 μg/kg body weight, preferably, from about 100 to about 400 μg/kg body weight.

In certain embodiments, the cell is a neoplastic cell, including but not limited to one derived from or characterized as being a pancreatic cancer, squamous cell carcinoma, breast cancer, colorectal cancer, renal cancer, brain cancer, prostate cancer, bladder cancer, bone cancer, joint cancer, uterine cancer, cervical cancer, endometrial cancer, multiple myeloma, Hodgkin's disease, non-Hodgkin's lymphoma, melanoma, leukemias, lung cancer, ovarian cancer, gastrointestinal cancer, Kaposi's sarcoma, liver cancer, pharyngeal cancer and laryngeal cancer.

In a preferred embodiment, the neoplastic cell is derived from or characterized as being squamous cell carcinoma, such as squamous cell carcinoma of the head and neck (SCCHN). In another preferred embodiment, the neoplastic cell is derived from or characterized as a pancreatic carcinoma cell such as a pancreatic adenocarcinoma cell.

By controlling cell proliferation, methods of the present invention can be useful in modulating or treating conditions, such as injured tissues or organs, grafting transplanted tissues, and the like by inducing or increasing/enhancing cell growth and/or proliferation.

Accordingly, in one particular embodiment of the present invention, the cell is a normal animal cell and the modulation or treatment of the condition results in an increased normal cell growth or proliferation by decreasing, disrupting or inhibiting OGFr expression in the cell to be modulated or treated. For example, the present invention provides a method for up regulating or growing skin cells in culture for a subject suffered from a burn or other tissue or organ injuries by decreasing, disrupting or inhibiting OGFr expression in the skin cells. Various methods for decreasing, disrupting or inhibiting OGFr expression in a cell are known and available in the art including, but not limited to, gene silencing (e.g., by DNA methylation or RNA interference, i.e., using small interfering RNA (siRNA)/short hairpin RNA (shRNA), antisense technology, antibody blockade of proteins, and genetic manipulation (e.g., knockout models). See, also, Example 4 and FIG. 9, which illustrate OGF modulation of normal cells (Normal Human Neo-Epidermal Keratinocyte cells (NHEK)).

In a particular embodiment, a method for assessing an anti-tumor treatment is provided according to the present invention which includes assaying at least a portion of a tumor for an increase in expression of at least one CDK inhibitor following administration of OGF to a subject having the tumor. An assaying kit for assessing an anti-tumor treatment is also contemplated by the present invention which includes OGF and components or reagents for detecting CKI expression, e.g., primers for PCR reaction, antibodies and reagents for Western Blotting, and probes and reagents for Southern and Northern blotting.

In another embodiment, the present invention is directed to a method for screening the eligibility of a subject for opioid growth factor (OGF) modulation or treatment of a cell proliferation or growth related condition by assessing the level of OGF receptor (OGFr) and the relevant cyclin dependent kinase inhibitor (CKI) in the cell to be modulated or treated, wherein the cell having at least one molecule of OGFr and at least one molecule of the CKI indicates the subject's eligibility.

According to the present invention, an animal cell, either a neoplastic cell or a normal cell, for OGF therapy, treatment or modulation should be determined whether such cell will exhibit therapeutic effects upon the administration or elimination of OGF-OGFr axis. These effects include, but are not limited to, slowed or delayed cell growth upon stimulation of the OGF-OGFr axis and an increased cell growth or proliferation upon disruption, inhibition or decreasing of OGFr expression. According to the present invention, the method includes the step or steps of screening a cell of interest for the expression of one or more particular relevant CDK inhibitors, such as p16 and/or p21, and OGFr. For example, if the cell is a SCCHN cell that expresses p16 and has OGFr, it will be identified as a cell that will be responsive to (i.e., whose cell growth and/or division will be delayed by) OGF therapy. Similarly, as shown herein, pancreatic carcinoma cells, which do not express p16, express p21 that is induced by OGF-OGFr signaling. Thus, a pancreatic cell carcinoma that is determined to express p21 and OGFr will be identified as a cell that will be responsive to OGF therapy.

Methods for screening cells for CKI expression at the nucleic acid and/or protein levels are well known in the art (e.g., by polymerase chain reaction (PCR) amplification using primers specific for a particular relevant CDK inhibitor (see, e.g., Examples 1, 2), Northern, Southern or Western blotting techniques or any of a number of bioactivity assays known in the art). Any such method may readily be used to determine whether a cell, e.g., either a neoplastic or normal cell of interest, expresses a particular or relevant CKI.

Likewise, to determine whether a cell, e.g., a neoplastic cell of interest, expresses OGFr, a number of well-known assays described in the art may be performed. See, e.g., Examples 2 and 3. Radioimmunoassays such as ELISAs and other competitive inhibition assays using labeled OGF and/or OGF-OGFr inhibitors (such as naloxone HCl, naltrexone HCl, and related salts and/or other derivative compounds thereof) can be used to detect and/or measure OGFr. In addition, immunofluorescence and other immuno-based assays may be performed using OGFr-specific antibodies, such as those that have been reported (Zagon et al., *Brain Res Brain Res Rev.* 38(3):351-76 (2002)).

In a particular embodiment, a method for assessing a tumor is provided. The method includes assaying at least a portion of a tumor for both OGFr expression and for expression of at least one CDK inhibitor.

Such a method may use any of various methods for assaying for OGFr and CDK inhibitor expression. Exemplary methods include assay of RNA encoding OGFr or CDK inhibitor. Such methods illustratively include RT-PCR (see, e.g., Examples 1 and 2), in-situ hybridization and Northern blot. In further embodiments, methods according to the present invention include assay of OGFr and/or CDK inhibitor protein. Such methods illustratively include immunoblotting, immunoprecipitation and immunohistochemistry.

A method for assessing a tumor according to the present invention allows for selection of an appropriate anti-tumor treatment method. Identification of a tumor as expressing OGFr and a relevant CKI which is up-regulated by OGF-OGFr axis is indicative of a tumor inhibited by administration of an effective amount of OGF.

In general, a tumor is assessed by obtaining a sample of the tumor for use in assays of OGFr and CDK inhibitor expression.

According to the present invention, the relevant CDK inhibitor (CKI) includes, but is not limited to, p15, p16, p18, p19, p21, p27 and p57. If the cell is one that expresses p16 and has OGFr, for example, it will be identified as a cell that will be responsive to (i.e., whose cell growth and/or division will be delayed by) OGF therapy. One such exemplary cell is a squamous cell carcinoma cell, such as SCCHN. Similarly, if the cell is one that does not express p16 but does express p21 and has OGFr, it will be identified as a cell that will be responsive to OGF therapy. One such exemplary cell is a pancreatic carcinoma cell.

In still another embodiment, the present invention is directed to a method for enhancing the efficacy of opioid growth factor (OGF) modulation or treatment of a cell growth or proliferation related disorder in a subject by increasing or enhancing the level of the relevant cyclin dependent kinase inhibitor (CKI) in the cell to be modulated or treated and administering to the subject an effective amount of OGF.

Methods of inducing, enhancing or increasing the level of the relevant CKI expression in a cell are well known in the art. For example, McConnell et al. (Induced Expression of p16INK4a Inhibits Both CDK4- and CDK2-Associated Kinase Activity by Reassortment of Cyclin-CDK-Inhibitor Complexes, *Molecular and Cellular Biology*, March 1999, p. 1981-1989, Vol. 19, No. 3) described regulating expression of $p16^{INK4a}$ tumor suppressor protein by addition or removal of isopropyl-$^{\beta}$-D-thiogalactopyranoside. See, e.g., Higuchi et al., Head and Neck 29:940-947, 2007; Lee and Yang, Cell Mol Life Sci 58(12-13):1907-1922, 2001; Grau et al., Cancer Res. 57(18):3929-3934, 1997.

In a particular embodiment, the method further includes enhancing the expression of the OGF receptor (OGFr) in the cells to be modulated or treated. OGFr expression can be induced or enhanced by methods known in the art, e.g., by using imiquimod/Aldara. See Urosevic et al, Clin. Cancer Res. 10:4959-4970, 2004.

In yet another embodiment, the present invention is directed to a method for enhancing the efficacy of opioid growth factor (OGF) modulation or treatment of a cell growth or proliferation related disorder in a subject, comprising enhancing the expression of the OGF receptor (OGFr) in the cells to be modulated or treated, and administering to the subject an effective amount of OGF. In a particular embodiment, the method further includes increasing the level of the relevant cyclin dependent kinase inhibitor (CKI) in the cells to be modulated or treated.

In still yet another embodiment, the present invention is directed to a method for monitoring the sensitivity or efficacy of opioid growth factor (OGF) modulation or treatment of a cell growth or proliferation related disorder in a subject, comprising assessing the level of retinoblastoma (Rb) protein phosphorylation in the subject.

Such a method may use any of the various methods for assaying retinoblastoma (Rb) protein phosphorylation. For example, phosphorylation of Rb can be detected by indirect immunofluorescence using a phosphospecific primary antibody against the particular phosphorylation site, e.g., serine 780 ($S^{780}$), and secondary antibodies conjugated to a fluorescence agent, such as Alexa Fluor 488.

A further embodiment of the present invention provides a method for treating a non-cancerous disease related to aberrant cell growth and proliferation in a subject, comprising administering to the subject an effective amount of OGF, wherein the cell to be treated comprises at least one an opioid growth factor receptor. See, e.g., Blebea et al. (Opioid growth factor modulates angiogenesis. J. Vascular Surg. 32:364-373, 2000), Blebea et al. (Differential effects of vascular growth factors on arterial and venous angiogenesis. J. Vasc. Surg. 35:532-538, 2002) and Zagon et al. (Opioid growth factor inhibits intimal hyperplasia in balloon-injured rat carotid artery. J. Vasc. Surg. 37:636-643, 2003).

While methods for treating cancers and tumors are envisioned by the present invention, methods for modulating CDK inhibitory pathways and/or Rb activity levels will be beneficial for treating a variety of cell growth and proliferation related disorders, conditions and/or diseases. Thus, for example, the present invention also provides methods for treating proliferative and/or differentiative disorders which arise from cells characterized by aberrant growth control which nonetheless require one or more CDKs (e.g., CDK4/6 or CDK2) for cell growth. There are a wide variety of pathological cell proliferative conditions for which methods of the present invention can provide therapeutic benefits by means of inhibiting aberrant cell proliferation. For instance, methods of the present invention can be used to treat various cancers and leukemias, psoriasis, bone diseases, fibroproliferative disorders such as involving connective tissues, atherosclerosis and other smooth muscle proliferative disorders, as well as chronic inflammation.

Methods of the invention will also be useful for treating proliferative disorders, differentiative disorders that result in whole or in part from, for example, de-differentiation of tissue which may be accompanied by abortive re-entry into mitosis. Such degenerative disorders include, but are not limited to, chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders which can be treated using methods of the present invention include, but are not limited to, disorders associated with connective tissue, such as may occur due to de-differentiation of chondrocytes or osteocytes, as well as vascular disorders which involve de-differentiation of tissues, such as of endothelial tissue and smooth muscle cells; certain gastric ulcers characterized by degenerative changes in glandular cells, and certain renal conditions marked by failure to differentiate, e.g. Wilm's tumors. Moreover, treatments involving development and maintenance of tissues and organs can also benefit from the methods of the present invention.

Methods of the present invention can also be useful in treating certain inflammatory and immune disorders, including, but not limited to, chronic inflammatory diseases and disorders, such as Crohn's disease, reactive arthritis, including Lyme disease, insulin-dependent diabetes, organ-specific autoimmunity, multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis. See, e.g., Zagon et al. (The opioid growth factor, [$Met^5$]-enkephalin, and the ζ (zeta) opioid receptor are present in human and mouse skin and tonically act to inhibit DNA synthesis in the epidermis, *J. Invest. Dermatol.* 106:490-497, 1996) as well as Example 5 (treatment of Rabbit Tenon's Fibroblasts in glaucoma).

One embodiment of the present invention provides a method for delaying the onset of tumorigenesis in an animal cell containing an opioid growth factor receptor. The method comprises the step of administering to the cell an effective amount of OGF in combination with at least one relevant CDK inhibitor. In certain preferred aspects, the relevant CDK inhibitor includes, but is not limited to, p15, p16, p18, p19, p21, p27 and p57.

Another embodiment of the present invention provides a method for slowing the progression of tumorigenesis in an animal cell comprising an opioid growth factor receptor. The method comprises the step of administering to the cell an effective amount of OGF in combination with at least one relevant CDK inhibitor. In certain preferred aspects, the relevant CDK inhibitor includes, but is not limited to, p15, p16, p18, p19, p21, p27 and p57.

Still another embodiment of the present invention provides a method for treating a hyperproliferative disorder, the progression of tumorigenesis, an inflammatory disorder or an immune disorder, characterized by aberrant cell proliferation. The method comprises the step of administering to the cell OGF in combination with at least one relevant CDK inhibitor in an animal cell comprising an opioid growth factor receptor. In certain preferred aspects, the CDK inhibitor includes, but is not limited to, p15, p16, p18, p19, p21, p27 and p57.

According to the present invention, the compositions comprising an effective amount of OGF may be formulated into compositions having a variety of forms. The compositions of the present invention will be administered at an effective dose to induce the particular type of tissue at the treatment site selected according to the particular clinical condition addressed. Determination of a preferred pharmaceutical formulation and a pharmaceutically and therapeutically efficient/effective dose regiment for a given application is well within the skill of the art taking into consideration, for example, the administration mode, the condition and weight of the patient, the extent of desired treatment and the tolerance of the patient for the treatment. The composition can also include at least one pharmaceutically additive, carrier, or adjuvant that is suitable for administering OGF and/or CKI to the subject or animal. The present invention also contemplates administering OGF and/or CKI with a suitable pharmaceutically additive, carrier, or adjuvant.

By "pharmaceutically acceptable carrier" is meant a carrier that is conventionally used in the art to facilitate the storage, administration, and/or the healing effect of the agent. A carrier may also reduce any undesirable side effects of the agent. A suitable carrier should be stable, i.e., incapable of reacting with other ingredients in the formulation. A suitable pharmaceutically carrier should not produce significant local or systemic adverse effect in recipients at the dosages and concentrations employed for treatment. A pharmaceutically acceptable carrier of the present invention is one that is suitable for animal, particularly, human, administration and does not include compounds that are utilized in animal toxicological studies. Such carriers are generally known in the art.

Suitable carriers for the present invention include those conventionally used, but are not limited to, albumin, gelatin, collagen, polysaccharide, monosaccharides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), and the like.

Water, saline, aqueous dextrose, and glycols are preferred liquid carriers, particularly (when isotonic) for solutions. The carrier can be selected from various oils, including, but not limited to, those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions of the present invention can be subjected to conventional pharmaceutical expedients, such as sterilization, and can contain conventional pharmaceutical additives, such as preservatives, stabilizing agents, wetting, or emulsifying agents, salts for adjusting osmotic pressure, buffers, and the like.

Doses expected to be suitable starting points for optimizing treatment regiments are based on the results of in vitro, ex vivo and/or in vivo assays. Based on the results of such assays, a range of suitable OGF concentrations can be selected to test at a treatment site in animals and then in humans.

The effective amount of OGF that can be administered according to the present invention for an intravenous therapy is between about 20 to about 1000 μg/kg body weight per day, preferably about 100 to about 400 μg/kg body weight per day. OGF may be administered at least three times a week, and as frequently as once daily, throughout the entire treatment period. OGF is safe and nontoxic and may be administered in essentially any amount necessary to be effective.

The effective amount of OGF may be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application and may be selected by one skilled in the art. Modes of administration may include systemic such as oral, parenteral (such as subcutaneous, intravenous, intraarterial, intralesional, intraosseous, intramuscular, intradermal, transdermal, transmucosal and inhalational), intraperitoneal, topical or local administration. The compositions may be formulated in dosage forms appropriate for each route of administration.

As the skilled artisan will appreciate, lower or higher doses than those recited may be required. Specific dosage and treatment regimens for any particular patient will depend upon a variety of factors, including the activity of OGF, the age, body weight, general health status, sex, diet, time of administration, rate of excretion, drug combination, the severity of the tissue damage and the judgment of the treating physician.

Methods for administering CDKs and CDK inhibitors have been described. Many are based on available nucleic acid delivery systems known to the skilled artisans. See, e.g., U.S.

Pat. Nos. 5,672,508, 5,981,702, 6,043,030, 6,255,071, 6,211,334, 6,290,951, and 6,858,709.

The following examples are provided to describe the invention in more detail. They are intended to illustrate, not to limit the present invention in any way.

Example 1

Detection of OGFr and p16 Expression by RT-PCR

A surgically excised sample of a squamous cell carcinoma of the head and neck (SCCHN) is subjected to RT-PCR in order to determine whether OGFr and p16 are expressed by tumor cells. RT-PCR detection of OGFr is performed as described in Zagon, I., et al., Neuropeptides, 2003, 37(5):290-7. Specific primers directed to OGFr useful in PCR of reverse transcribed mRNA include the following:

```
hu-ogf-r-5'
                                        (SEQ ID NO: 1)
5'-gtagaattcCCGCCGAGCATGGACGACCCCGACT-3'

hu-ogf-r-3'
                                        (SEQ ID NO: 2)
5'-ttaTCTAGAttaTTAAGGCTTCCCAGACTTGGCAGA-3'
```

RT-PCR detection of p16 was performed as described in Schneider S. et al., Methods Mol Biol., 2004, 281:91-103; Asamoto M. et al., Jpn J Clin Oncol. 1997, 27(1):22-5; or Quentin T. et al., Anticancer Res., 2004, 24(2B): 1011-23.

Example 2

The OGF-OGFr Axis Utilizes the P16 Pathway to Inhibit Head and Neck Cancer

The SCC-1 (UM-SCC-1) cell line was obtained from the University of Michigan Cancer Research Laboratory, and CAL-27 and SCC-4 cells were obtained from the American Type Culture Collection (Manassas, Va.). SCC-1 and CAL-27 cells were cultured in DMEM media, whereas SCC-4 cells were grown in 1:1 Hams F-12 DMEM media. All media was supplemented with 10% fetal bovine serum (HyClone, Logan, Utah), 1.2% sodium bicarbonate, and 5000 units/ml penicillin, 5 μg/ml streptomycin and 10 μg/ml neomycin. OGF was purchased from Sigma-Aldrich (St. Louis, Mo.), dissolved in sterile water, and used at a final concentration of $10^{-6}$ M.

Cell growth and flow cytometry. For growth curves, cells were seeded in 6-well plates at an initial density of ~$2\times10^5$ cells/well. Fresh media and OGF were added 24 h after initial seeding, and media and OGF were replaced daily. At appropriate times, the cells were washed with PBS, trypsinized, and viable cell numbers were counted by trypan blue exclusion using a hemacytometer.

For flow cytometry, cells were synchronized with 0.5 μg/ml nocodazole (Sigma-Aldrich) for 24 h, followed by three washes with complete media. Cells were released from growth arrest by addition of complete media or OGF-supplemented media. Synchronized cells were treated with $10^{-6}$ M OGF for 14 h, harvested with 0.25% trypsin-EDTA (Mediatech, Herndon, Va.) and fixed with 70% ethanol at −20° C. for up to 7 days before DNA analysis. DNA content was obtained by incubating cells in PBS containing propidium iodide (0.1 mg/ml) and RNase A (0.02 mg/ml) for 15 min at 22° C. Fluorescence was measured and analyzed using a BD Biosciences FACScan flow cytometer (San Diego, Calif.) and Modfit Software (Topsham, Me.).

siRNA knockdown of OGFr. The OGFr-targeted siRNAs (antisense:5'-uagaaacucagguuuggcg-3' (SEQ ID NO:3); sense: 5'-cgccaaaccugaguuucua-3' (SEQ ID NO:4)) were designed and obtained as ready-annealed, purified duplex probes from Ambion (Austin, Tex.). For transfection, 5×104 cells per well were seeded in 6-well plates containing 1 ml of serum-containing media without antibiotics. In each well, 20 nM OGFr-siRNA or control siRNA solutions in serum-free media were added. Cells were incubated for 4 h at 37° C. prior to the addition of OGF. Cultures were incubated an additional 20 h, and then 1 ml fresh complete media either lacking or containing OGF was added. At 96 h, cells were collected for computing growth. Two independent experiments were conducted. The control siRNAs were purchased from Ambion.

Synchronized cells (~$2\times10^6$) from each treatment were solubilized in 200 μl RIPA buffer (1×PBS, 10 μM IGEPAL, 1 mg/ml SDS, 5 mg/ml deoxycholic acid), containing protease and phosphatase inhibitors (2 μg/ml aprotinin, 3 mg/ml phenylmethyl sulfonyl fluoride (PMSF), 1 mM sodium orthovanidate, 1 μM okadaic acid). Total protein concentrations were measured using the DC protein assay kit (Bio-Rad Laboratories, Hercules, Calif.). Equal amounts of protein (40 μg) were subjected to 10% SDS-PAGE followed by transfer of proteins onto polyvinylidene difluoride (Millipore, Billerica, Mass.) using standard protocols. The following antibodies were purchased from commercial sources: phospho-Rb (Ser795), phospho-Rb (Ser807/811) (Cell Signaling Technology, Beverly, Mass.); phospho-Rb (Thr821) (Biosource, Camarillo, Calif.); Cdk4, cyclin D1, p15, p16, p18, p19 (Santa Cruz Biotechnology, Santa Cruz, Calif.); total Rb, p21, p27 (BD PharMingen, San Diego, Calif.); β-actin (Clone AC-15, Sigma). The following dilutions of primary antibodies were used to detect respective proteins. 1:200 phospho-Rb (Ser795), 1:200 phospho-Rb (Ser807/811); 1:200 phospho-Rb (Thr821); 1:200 Cdk4, 1:200 cyclin D1, 1:100 p16; 1:200 total Rb, 1:200 p21, 1:100 p27. Membranes were probed with secondary anti-rabbit or anti-mouse horseradish peroxidase-conjugated antibodies (GE Healthcare-Amersham Biosciences, Piscataway, N.J.); blots were developed using a chemiluminescence Western blotting detection system (GE Healthcare-Amersham Biosciences).

To determine equal loading of total protein samples, blots were reprobed with monoclonal antibody against β-actin at a dilution of 1:2000. If necessary, membranes were stripped in stripping buffer (62.5 mM Tris-HCl and 100 mM β-mercaptoethanol/2% SDS, pH 6.7) at 50° C. before being re-probed. Means and SE were determined from 3 or more independent experiments.

To quantify expression levels or kinase activity, the optical density of each band was determined by densitometry and analyzed by QuickOne (Bio-Rad Laboratories). Each value was normalized to β-actin from the same blot. To report the changes due to OGF treatment, the fold increase was calculated by dividing the normalized value from the OGF treated samples by the normalized value of control samples at each time point; thus, increases due to OGF have values greater than one, and decreases due to OGF have values less than one.

Immunoprecipitation and Rb kinase assay. For immunoprecipitating protein complexes, cell extracts were prepared as follows: $2\times10^6$ cells per sample were rinsed in cold PBS followed by lysis in 100 μl NP40 immunoprecipitation buffer (1% NP-40, 50 mM Tris-HCI (pH7.4), 150 mM NaCl, 1 mM EDTA, 10 mM NaF, 2 μg/ml antipain, 1 mM sodium orthovanidate, 2 μg/ml aprotinin, 2 μg/ml leupeptin, 1 μg/ml pepstatin A, 1 μM okadaic acid, 1 mM PMSF, 1 mM dithiothreitol (DTT). For each immunoprecipitation reaction mixture, a total of 500 μg of protein extract was used. The lysates were then subjected to immunoprecipitation using 10 μl polyclonal antibody against Cdk4 prebound with agarose conjugate (sc-601 AC, Santa Cruz) for 60 min at 4° C. Then immunoprecipitates were mixed with kinase buffer (25 mM HEPES, pH7.4, 10 mM MgCl2), 5 μCi $\gamma^{32}$P-ATP, and Rb(769-921) (sc-4112, Santa Cruz) as the substrate for Cdk4. After incubation for 30 min at 30° C., with occasional mixing, the reaction was stopped by the addition of 2× sample loading buffer (0.5 M Tris-HCl, pH 6.8, 4.4% (w/v) SDS, 20% (v/v) glycerol, 2% (v/v) 2-mercaptoethanol, and bromophenol blue in distilled/deionized water). Proteins in the reaction mixture were separated by a 10% SDS-PAGE gel. The Cdk4 kinase activity pattern was visualized by autoradiography of phosphorylated Rb.

Cell extracts were subjected to immunoprecipitation using antibodies against Cdk4 and protein A beads (Santa Cruz). Immunoprecipitates were separated on a 15% SDS-PAGE gel, and membrane blots probed with p16 antibodies (1:200), and developed using a chemiluminescence Western blotting detection system. Blots were re-probed with Cdk4 antibody (1:200). Five independent experiments were performed.

The p16-targeted siRNAs (antisense:5' acaccgcuucugc-cuuuucuu-3'; sense (SEQ ID NO:5): 5' gaaaaggcagaagcggu-guuu-3'(SEQ ID NO:6) were obtained as ready-annealed, purified duplex probes (Invitrogen, Carlsbad, Calif.). For transfection, $2\times10^5$ cells per well were seeded in 6-well plates containing 1 ml of serum-free media without antibiotics. In each well, 20 nM of p16-siRNA or control siRNA solutions in serum-free media were added. Cells were incubated for 4 h at 37° C. prior to the addition of OGF. Cultures were incubated for additional 20 h, and then 1 ml fresh complete media either lacking or containing OGF was added. At the indicated time points, cells were collected for growth curves or Western blotting. Three or more independent experiments were conducted. The control siRNAs were purchased from Ambion.

Values were assessed by one-way analysis of variance (ANOVA) and Newman Keul's post multiple comparison tests. Differences were considered statistically significant when $p<0.05$.

Continuous exposure to exogenous OGF inhibited the growth of SCC-1 human SCCHN cells. Cell number in the OGF-treated wells was 87.5% compared to controls at 72 h, and 59.0% of controls at 96 h. Linear regression analysis of the data revealed mean doubling times for the OGF and control groups of approximately 41.3 and 21.6 h, respectively, and differed from each other at $p<0.001$.

To examine the specificity of OGF for OGFr, knockdown experiments with OGFr-siRNA were conducted. Exposure to $10^{-6}$ M OGF depressed the growth of wt and control siRNA-treated cells by 29% and 46%, respectively, whereas $10^{-6}$ M NTX increased the number of wt and control siRNA-exposed cells by 24% and 27%, respectively. SCC-1 cells subjected to OGFr-siRNA had approximately 19% more cells than wt and control siRNA-treated cultures. In contrast to cells expressing OGFr, exposure to $10^{-6}$ M OGF or NTX had no further effects on the OGFr-siRNA cultures.

Based on growth curves, the effect of OGF on cell cycle distribution was analyzed by flow cytometry. The percentage of OGF-treated cells in the $G_0/G_1$ phase was 34.6% compared to 21.9% of the control cells; this increase in the number of cells in the $G_0/G_1$ phase was significantly ($p<0.001$) different from sterile water control values. Correspondingly, the number of OGF-exposed cells in the S phase decreased to 42.7% relative to 51.9% of the sterile water treated cells. The number of cells subjected to OGF in the G2/M phase was 22.7% in relationship to 26.2% for control samples.

OGF treatment does not change total Rb protein but decreases the amount of phosphorylated Rb (pRb). The phosphorylation of Rb protein is necessary for cells to progress from G1 to the S phase. To elucidate the role of Rb in OGF-induced SCC-1 cell growth inhibition, Rb expression and the phosphorylated state of Rb were assessed in synchronized SCC-1 cells. Expression of total Rb protein was not decreased from baseline values or level after 14 h of OGF treatment. However, the level of phospho-Rb (Ser801/811), which is specifically phosphorylated by Cdk4 in the G1 phase, was significantly decreased after a 6, 9, and 12 hour exposure to $10^{-6}$ M OGF. Although phospho-Rb (pT821) was specifically phosphorylated by Cdk2 in the G1 phase, OGF treatment did not alter the results of Western blot analysis of phospho-Rb (pT821) levels. These results suggest that Cdk4 but not Cdk2 was involved in the OGF-induced cell cycle block at the G1 phase in SCC1 cells.

Total levels of p105 and p107, which are alternative pathways to Rb regulation, revealed no changes in basal levels of proteins after exposure to OGF.

To verify whether OGF-induced downregulation of pRb was associated with changes in Cdk4, Cdk4 expression and activity levels were determined. The expression of Cdk4 protein did not change following OGF exposure (FIG. 1). When Rb was used as substrate in immunoprecipitation experiments performed with antibodies against Cdk4, lysates from cells treated with OGF for 3 h showed a transient increase of Cdk4 kinase activity; at 6, 9, and 12 h, there was a marked decrease in Cdk4 kinase activities relative to controls (FIG. 1). These results suggest that OGF-mediated decrease of pRb was correlated with the reduction in Cdk4 kinase activities.

To examine whether the OGF-induced downregulation of Cdk4 kinase activity was based on a decrease in cyclin D1 expression, homogenates of SCC-1 cells were subjected to Cdk4 immunoprecipitation. Cyclin D1 protein levels were assessed by Western blotting. The level of the cyclin D1/Cdk4 complex after treatment with OGF revealed no change from control levels.

Figure 2:
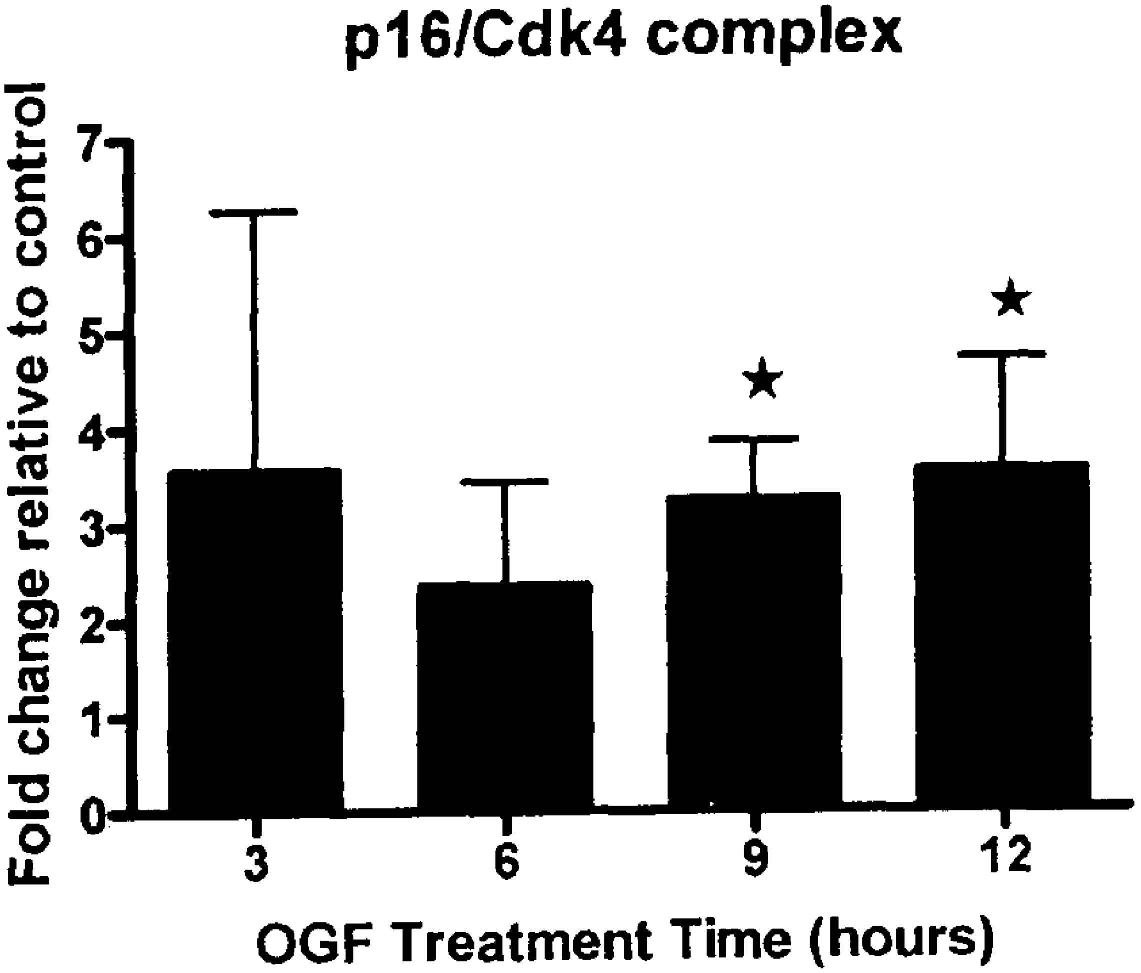
FIG. 2. OGF induced p16 expression. To examine whether the OGF-induced downregulation of Cdk4 kinase activity was based on p16/Cdk4 complex formation, homogenates of SCC-1 cells treated with OGF or sterile water were subjected to Cdk4 immunoprecipitation; the resulting proteins were blotted with antibodies to p16. Densitometric analysis of Western blots of immunoprecipitated p16/Cdk4 protein complex at 3, 6, 9, and 12 h revealed that p16 complexed to Cdk4 was increased at all time points, and was significantly different from control group at $p<0.05$ (*) at 9 and 12 h.

CDK inhibitor p16 expression is upregulated by OGF. Cell cycle progression depends on both positive and negative regulators. Expression of p16 was evaluated in synchronized SCC-1 cells after 3, 6, 9, and 12 h of OGF exposure. p16 was significantly upregulated ($p<0.05$) in OGF-treated cells relative to control cells only at 3 h. Because p16 inhibits Cdk4 by physical interaction, whether the OGF-induced downregulation of Cdk4 kinase activity was based on p16/Cdk4 complex formation was investigated. To explore this possibility, homogenates of SCC-1 cells were subjected to Cdk4 immunoprecipitation, and the precipitated proteins were probed with p16 antibodies. The level of the p16/Cdk4 complex following OGF treatment was elevated at all time points compared to control, and reached statistical significance ($p<0.05$) at 9 and 12 h (FIG. 2).

Figure 3:
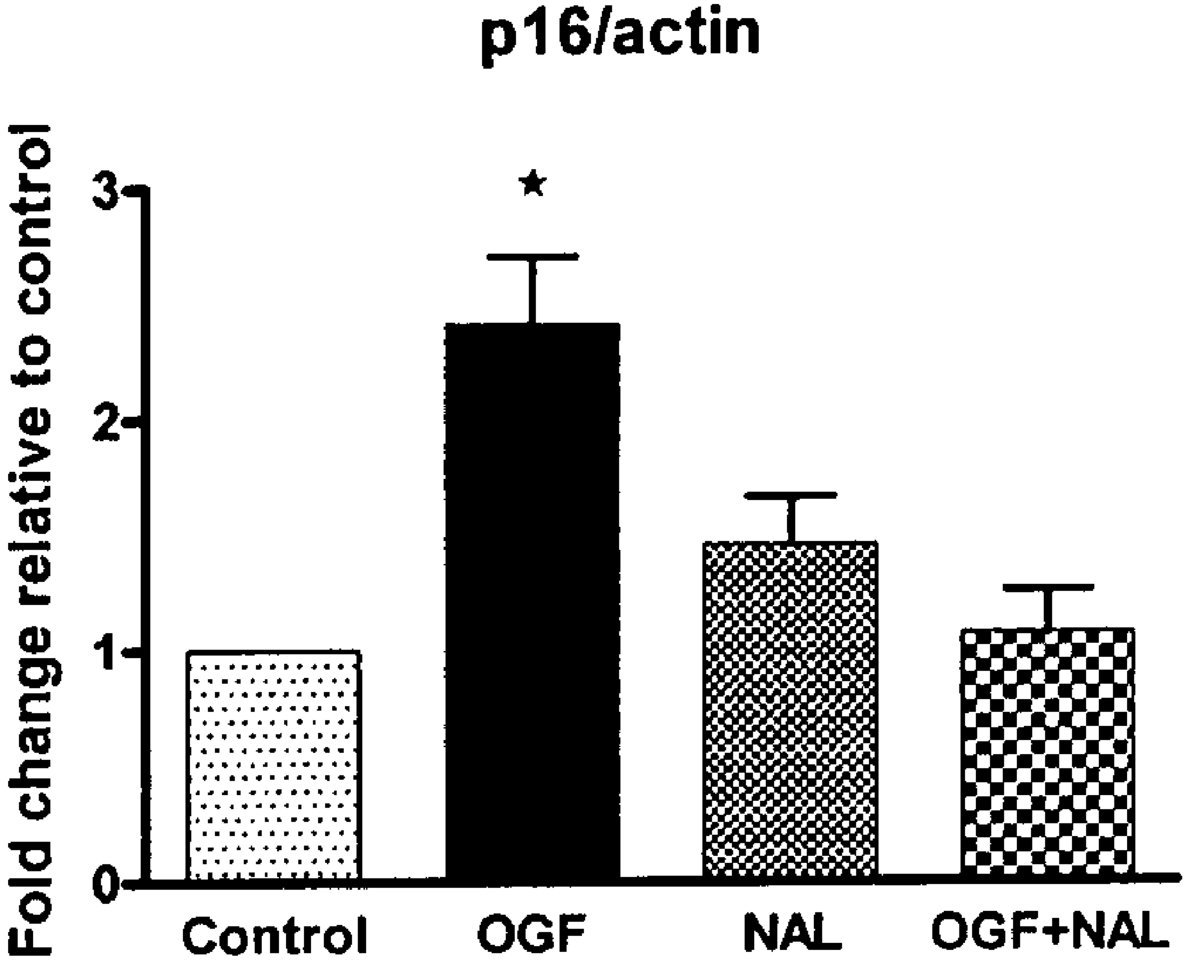
FIG. 3. To examine for opioid receptor mediation, synchronized cells were treated with $10^{-6}$ M OGF, $10^{-5}$ M naloxone (NAL), both OGF and NAL, or sterile vehicle (Control) for 3 h. Protein lysates were resolved on SDS-PAGE, and subjected to Western blot analysis for p16 and actin. Densitometric analysis of p16 expression showed that p16 levels of OGF treated cells were significantly elevated from control levels at $p<0.05$ (*); no change was recorded in the NAL and OGF-NAL groups. Data represent means±SE for 3 independent experiments.

To demonstrate the opioid-receptor mediation of OGF, cells were treated concomitantly with the opioid antagonist naloxone and OGF. OGF-induced upregulation of p16 expression was blocked in cells exposed to both naloxone and OGF; naloxone alone had no effect on p16 expression (FIG. 3). This result showed that OGF-induced upregulation of p16 expression was receptor-mediated. p16 is known as a tumor suppressor gene, functioning as a cell cycle inhibitor by forming heterotrimeric complexes with Cdks and cyclins. Therefore, the data suggest that under the effect of OGF, p16 protein level was upregulated, and activated the p16-Rb pathway that, in turn, mediated the cell cycle block.

Figure 4A:
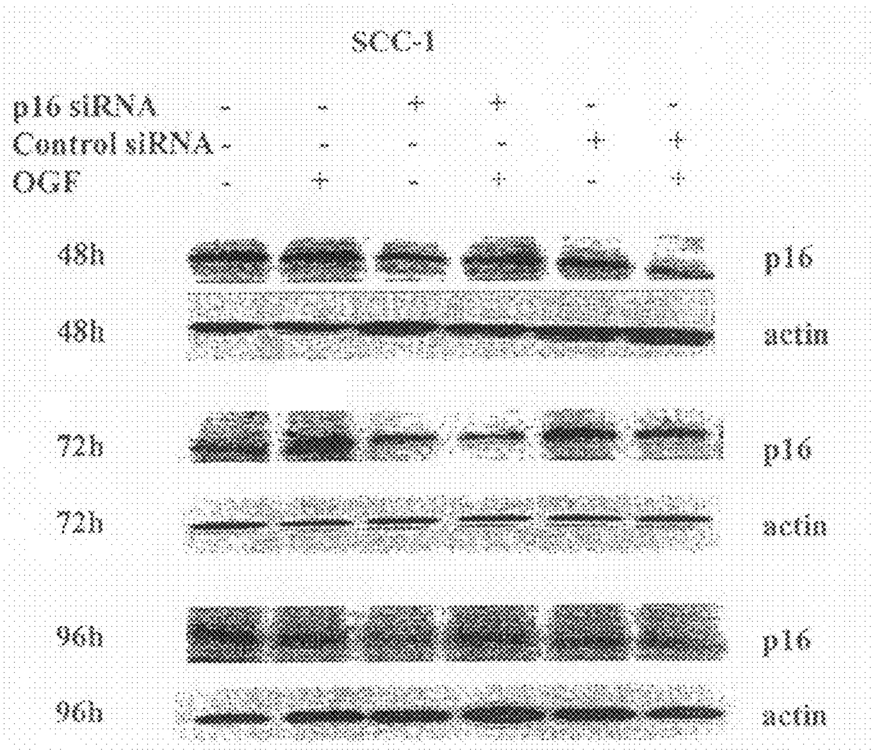
FIGS. 4A-4C. p16 is required for OGF-induced growth inhibition. SCC-1 cells were transfected with p16 siRNAs or control siRNAs for 48, 72, or 96 h. Total proteins were isolated and separated by SDS-PAGE, and probed with antibodies specific to p16 or actin. Growth curves for SCC-1 cells transfected with either p16 siRNA or negative control siRNA, and grown in the presence or absence of $10^{-6}$ M OGF for 96 h. Cells were harvested at 48, 72, and 96 h, and counted with a hemacytometer. Data represent means±SE for 3 independent experiments. Cell numbers for OGF-treated cells were significantly reduced from control levels at $p<0.05$ (*).
Figure 4B:
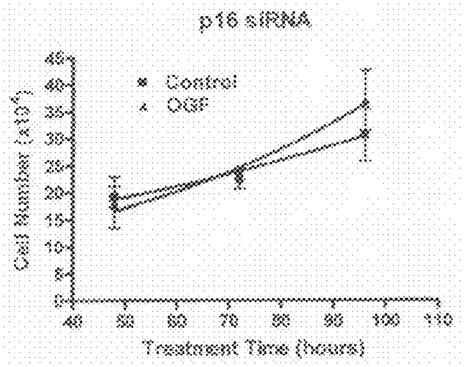
Figure 4C:
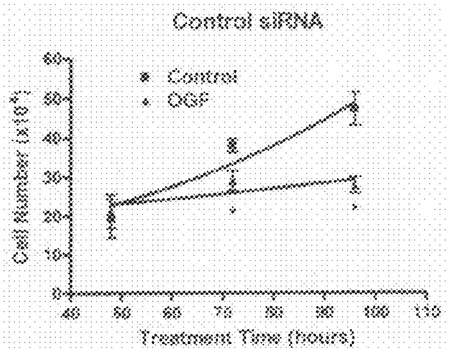

Analysis of the expression of cell cycle inhibitors p15, p18, p19, p21 and p27 revealed that OGF treatment of SCCHN had no significant effect on these CKIs. No p57 protein was detected in SCC-1. Thus, OGF treatment results in the induction of only p16 in SCCHN.

siRNA directed against p16 blocked OGF inhibitory action. To test the role of p16 in OGF-induced inhibitory action on SCC1 cell growth, siRNA knockdown experiments were performed. SCC1 cells were treated with p16 siRNA or with negative control siRNA. Western blot analysis revealed that cells transfected with p16 siRNA had significantly reduced levels of p16 protein compared to untransfected cells after 72 h (FIG. 4A). Growth analysis of cells transfected with p16 siRNAs and subsequently exposed to OGF for 96 h, showed that p16 induction is required for the OGF inhibitory action on SCC-1 cell growth (FIG. 4B). SCC-1 cells transfected with the negative control siRNAs and exposed to OGF had significant reductions in growth of 24% and 40% at 72 and 96 h, respectively. See FIG. 4C.

The siRNA used in accordance with the present invention are available in the art. One skilled in the art can also design and synthesize siRNAs based on the sequence information of CKIs and OGF/OGFr, which information is available in the art. For example, the p16-targeted siRNAs (antisense:5' acaccgcuucugccuuuucuu-3' (SEQ ID NO: 5); sense: 5' gaaaaggcagaagcgguguuu-3' (SEQ ID NO: 6) (Zhou et al., Rheumatology 43:555-568, 2004) used herein were obtained as ready-annealed, purified duplex probes (Invitrogen, Carlsbad, Calif.). The control siRNA was obtained from AMBION. The p21 siRNA was obtained from Santa Cruz Biotechnology.

To examine the ubiquity of the integral role of p16 inhibition, two other SCCHN cell lines were examined: CAL-27 and SCC-4. In synchronized CAL-27 cells, OGF increased p16 expression at 9 h relative to controls. Western blot analysis of protein isolated from CAL-27 cells transfected with p16 siRNA had significantly reduced p16 levels relative to control cells. Growth curves revealed that OGF had no inhibitory effects on CAL-27 cells lacking p16. In another cell line, SCC-4, OGF treatment induced p16 expression at 3 h relative to synchronized control cells. Protein isolated from SCC-4 cells transfected with p16 siRNAs and analyzed by Western blot showed significantly reduced levels of p16 protein compared to control cells at 72 h. Growth curves of these SCC-4 cells showed that OGF had no effect on cells lacking p16 expression, but that OGF significantly ($p<0.05$) inhibited (a decrease of 43%) the growth of SCC-4 cells transfected with negative control siRNAs for 96 h.

Example 3

The OGF-OGFR Axis Utilizes the p21 Pathway to Restrict Progression of Human Pancreatic Cancer Human pancreatic cancer cell lines BxPC-3, PANC-1, and Capan-2 were obtained from the American Type Culture Collection (Manassas, Va.), and cultured in RPMI, Dulbecco's Modified Medium, or McCoy's 5A medium, respectively. All media were supplemented with 10% fetal bovine serum, 1.2% sodium bicarbonate, and 0.25% antibiotics (5000 units/ml penicillin, 5 μg/ml streptomycin and 10 μg/ml neomycin). OGF was purchased from Sigma-Aldrich (St. Louis, Mo.), dissolved in sterile water, and used at a final concentration of $10^{-6}$ M.

For growth curves, cells were seeded in 6-well plates at an initial density of $2\times10^5$ cells/well. Fresh media and OGF were added 24 hours after initial seeding, and media and OGF were replaced daily. At appropriate times, the cells were washed with PBS, trypsinized, and viable cell numbers were counted by trypan blue exclusion using a hemacytometer.

For flow cytometry, cells were synchronized with 67 ng/ml nocodazole (Sigma-Aldrich) for 24 hours, followed by three washes with complete media. Cells were released from growth arrest by addition of complete media or OGF supplemented complete media. Synchronized cells were treated with 10-6 M OGF for 21 hours, harvested with 0.25% trypsin-EDTA (Mediatech, Herndon, Va.) and fixed with 70% ethanol at −20° C. for up to 7 days before DNA analysis.

DNA content was obtained by incubating cells in PBS containing propidium iodide (0.1 mg/ml) and RNase A (0.02 mg/ml) for 15 minutes at 220 C. Fluorescence was measured and analyzed using a BD Biosciences FACScan flow cytometer (San Diego, Calif.) and Modfit Software (Topsham, Me.).

Synchronized cells ($2\times10^6$) from each treatment were solubilized in 200 μl RIPA buffer (1×PBS, 10 μM IGEPAL, 1 mg/ml SDS, 5 mg/ml deoxycholic acid), containing protease and phosphatase inhibitors (2 μg/ml aprotinin, 3 mg/ml phenylmethyl sulfonyl fluoride, 1 mM sodium orthovanidate, 1 μM okadaic acid). Total protein concentrations were measured using the DC protein assay kit (Bio-Rad Laboratories, Hercules, Calif.). Equal amounts of protein (40 μg) were subjected to 10% SDS-PAGE followed by transfer of proteins onto polyvinylidene difluoride (Millipore, Billerica, Mass.) using standard protocols.

The following antibodies were purchased from commercial sources: phospho-Rb (Ser795), phospho-Rb (Ser807/811) (Cell Signaling Technology, Beverly, Mass.); Cdk2, p57 (Santa Cruz Biotechnology, Santa Cruz, Calif.); p21, p27, total Rb (BD PharMingen, San Diego, Calif.); β-actin (Clone AC-15, Sigma-Aldrich).

Membranes were probed with secondary anti-rabbit or anti-mouse horseradish peroxidase-conjugated antibodies (GE Healthcare-Amersham Biosciences, Piscataway, N.J.), and developed using a chemiluminescence Western blotting detection system.

To determine equal loading of total protein samples, blots were re-probed with monoclonal antibody against β-actin at a dilution of 1:2000. If necessary, membranes were processed in stripping buffer (62.5 mM Tris-HCI and 100 mM β-mercaptoethanol/2% SDS, pH 6.7) at 50° C. before being re-probed.

To quantify expression levels or kinase activity, the optical density of each band was determined by densitometry and analyzed by QuickOne (Bio-Rad Laboratories). Each value was normalized to β-actin from the same blot. To report the changes due to OGF treatment, we calculated the fold increase by dividing the normalized value from the OGF treated samples by the normalized value of control samples at each time point; thus, increases due to OGF have values greater than one, and decreases due to OGF have values less than one. For all Western blot analyses, 3 or more independent experiments were performed.

To immunoprecipitate protein complexes, cell extracts were prepared as follows: $2\times10^6$ cells per sample were rinsed in cold PBS followed by lysis in 200 μl immunoprecipitation buffer (1% NP-40, 10 mM HEPES (pH 7.5), 200 mM NaCl, 5 mM EDTA, 50 mM NaF, 0.2 mM sodium orthovanidate, 1 mM phenylmethyl sulfonyl fluoride, 2 mM dithiothreitol), 1× Halt™ protease inhibitorcocktail (Pierce, Rockford, Ill.)). For each immunoprecipitation reaction mixture, a total of 500 μg of protein extract was used. To each sample, 50 μl of protein A beads (Santa Cruz Biotechnology) were added and incubated at 40° C. for 30 min with rotation. Beads were removed by centrifugation at 14000 rpm for 15 s. The lysates were then subjected to immunoprecipitation using 10 μl of polyclonal antibody against Cdk2 and incubated at 40° C. for 1.5 hours with rotation, followed by addition of 20 μl of protein A beads as the immune complex binding agent.

Samples were further incubated at 40 C for 1 hour with rotation. Beads were pelleted by centrifugation at 14000 rpm for 15 s, washed three times with 500 μl ice-cold immunoprecipitation wash buffer (1% NP-40, 50 mM HEPES, 150 mM NaCl, 1 mM EDTA, 1 mM dithiothreitol), and followed by two washes with ice-cold H1 kinase buffer (50 mM HEPES (pH 7.5), 10 mM MgCl2, 10 mM MnCl2, 1 mM dithiothreitol). Immunoprecipitates were incubated with 10 μCi $\gamma^{32}$P-ATP, and 1 μg of histone H1 (Roche) as the substrate for Cdk2. After incubation for 30 min at 30° C., with occasional mixing, the reaction was stopped by the addition of 2× sample loading buffer (Santa Cruz Biotechnology). Proteins were separated by a 12% SDS-PAGE gel, and the Cdk2 kinase activity pattern was visualized by autoradiography of phosphorylated H1.

Cell extracts were subjected to immunoprecipitation using antibodies against Cdk2 and protein A beads. Immunoprecipitates were separated on a 15% SDSPAGE gel, and membrane blots probed with p21 antibodies (1:100), and developed using a chemiluminescence Western blotting detection system. Blots were reprobed with Cdk2 antibody (1:200).

The p21-targeted siRNAs were obtained from Santa Cruz Biotechnology, and negative control siRNAs were purchased from Ambion (Ambion, Inc., Austin, Tex.). For transfection, 2×105 cells per well were seeded in 6-well plates containing 1 ml of media without antibiotics. For each well, 1 μl of siRNA stock (20 μM) was mixed with 175 μl of serum-free media. Two μl of Oligofectamine reagent (Invitrogen, Carlsbad, Calif.) was added to prewashed cells in each well, making the final concentration for siRNA approximately 20 nM. Cells were incubated for 4 hours at 37° C. prior to the addition of OGF. Eighteen hours later, 1 ml fresh complete media with or without OGF was added to the cultures; media and OGF were replaced daily. At the indicated time points, cells were collected for growth curves or Western blotting.

Values were assessed by one-way analysis of variance (ANOVA) and Newman Keul's post multiple comparison tests.

Continuous exposure to exogenous OGF inhibited the growth of BxPC-3 human pancreatic cancer cells. At 48 and 72 hours, cell numbers in the OGF-treated wells were 66% and 55%, respectively, compared to control cultures receiving sterile water. Linear regression analysis of the data revealed mean doubling times for the OGF and control groups of 51 and 28 hours, respectively; these doubling times differed from each other at $p<0.01$.

Based on growth curves, the effect of OGF on cell cycle distribution by flow cytometry was analyzed. The percentage of OGF-treated cells in the G0/G1 phase was 69.1% compared to 55.1% of the control cells. Correspondingly, the number of OGF-exposed cells in S phase decreased to 28.0% relative to 44.8% of the sterile water control cells. The number of cells subjected to OGF in the G2/M phase was 2.9% in relationship to 0.1% for control samples.

The phosphorylation of Rb protein is necessary for cells to progress from G1 to the S phase. To elucidate the role of Rb in OGF-induced inhibition of BxPC-3 cell growth, Rb expression and the phosphorylated state of Rb were assessed in synchronized BxPC-3 cells. Expression of total Rb protein was not decreased from baseline values after 21 hours of OGF treatment using an antibody at 1:200 dilution. However, the level of phospho-Rb (Ser795), which is specifically phosphorylated by Cdk2 in the G1 phase, was decreased at 15, 18, and 21 hours following exposure to $10^{-6}$ M OGF, and reached statistical significance at 21 hours ($p<0.01$). Although phospho-Rb (pSer807/811) was specifically phosphorylated by Cdk4 in the G1 phase, OGF treatment did not alter the results of Western blot analysis of phospho-Rb (pSer807/811) levels. These results suggest that Cdk2, not Cdk4, was involved in the OGF induced cell cycle block at the G1 phase in BxPC-3 cells.

To verify whether the OGF-induced downregulation of pRb was associated with changes in Cdk2, Cdk2 expression and activity levels were determined. The expression of Cdk2 protein did not change following OGF exposure (FIG. 5). When H1 was used as a substrate in immunoprecipitation experiments performed with antibodies against Cdk2, lysates from cells treated with OGF for 15, 18 and 21 hours showed significant decreases of 78%, 46% and 82%, respectively, in kinase activities compared to sterile water treated control cultures (FIG. 5). These results demonstrate that the OGF-mediated decrease of pRb was consistent with the reduction in Cdk2 kinase activities.

To examine whether the OGF-induced downregulation of Cdk2 kinase activity was related to a change in cyclin E expression, homogenates of BxPC-3 cells were subjected to Cdk2 immunoprecipitation. Cyclin E protein levels were assessed by Western blotting. The level of the cyclin E/Cdk2 complex after treatment with OGF revealed no change from control levels.

Figure 6:
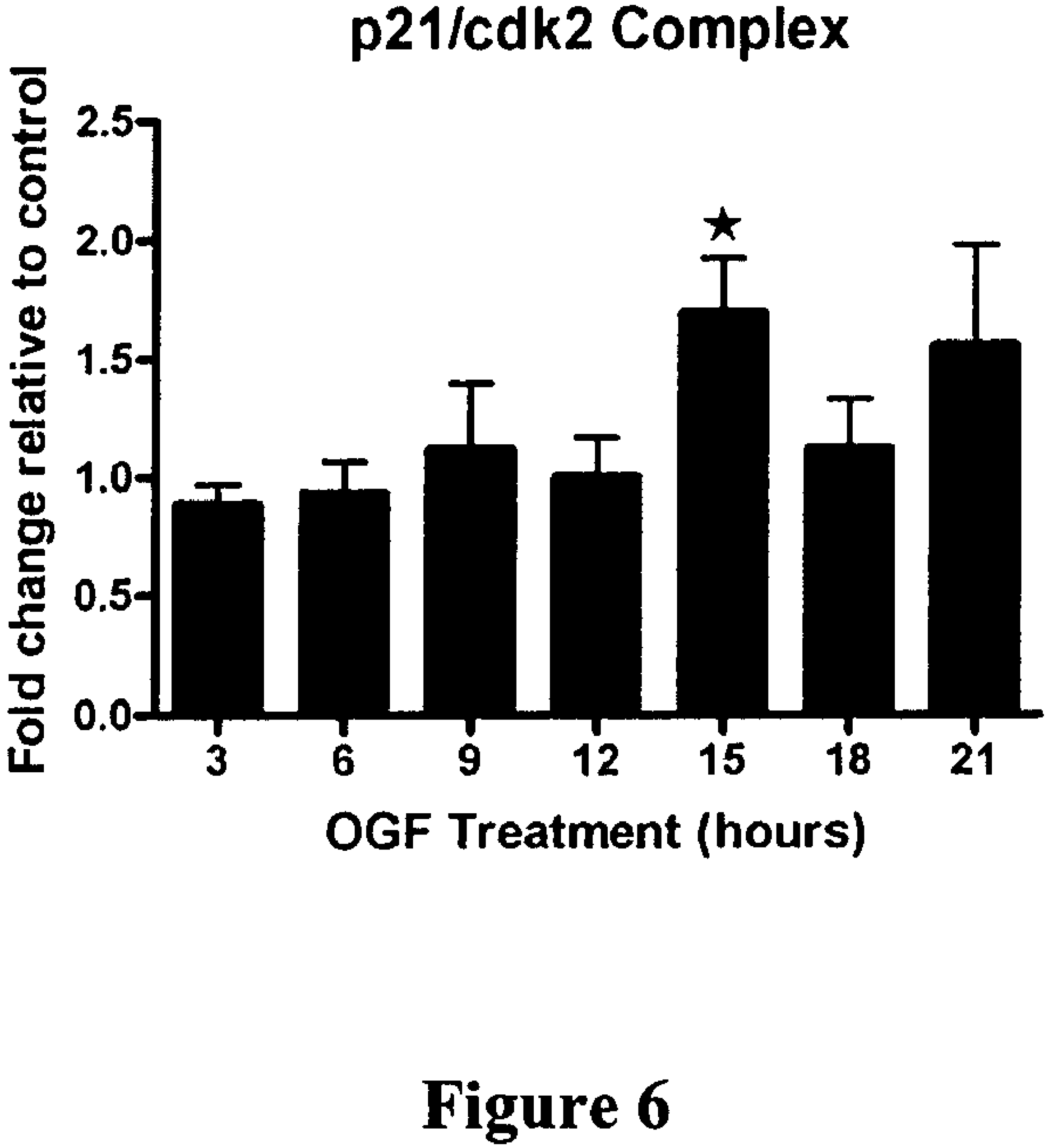
FIG. 6. OGF induced p21 expression. To examine whether the OGF-induced downregulation of Cdk2 kinase activity was based on p21/Cdk2 complex formation, homogenates of BxPC-3 cells treated with OGF or sterile water were subjected to Cdk2 immunoprecipitation; the resulting proteins were blotted with antibodies to p21. Densitometric analysis of Western blots of immunoprecipitated p21/Cdk2 complexed protein at 3, 6, 9, 12, 15, 18, and 21 hours revealed an increase at 9, 12, 15, 18, and 21 hours, with significant difference between the OGF and 15-hour control group (*$p<0.05$).

Expression of p21 was evaluated in synchronized BxPC-3 cells after 3, 6, 9, and 12 hours of OGF exposure. p21 was significantly upregulated ($p<0.05$) in OGF treated cells relative to sterile water control cells after 9 hours of drug treatment. Because p21 inhibits Cdk2 by physical interaction, whether the OGF-induced downregulation of Cdk2 kinase activity was based on p21/Cdk2 complex formation was evaluated. To explore this possibility, homogenates of BxPC-3 cells were subjected to Cdk2 immunoprecipitation, and the precipitated proteins were probed with p21 antibodies. The levels of the p21/Cdk2 complex following OGF treatment were elevated at all time points compared to control levels, and reached statistical significance ($p<0.05$) at 15 hours (FIG. 6).

Figure 7:
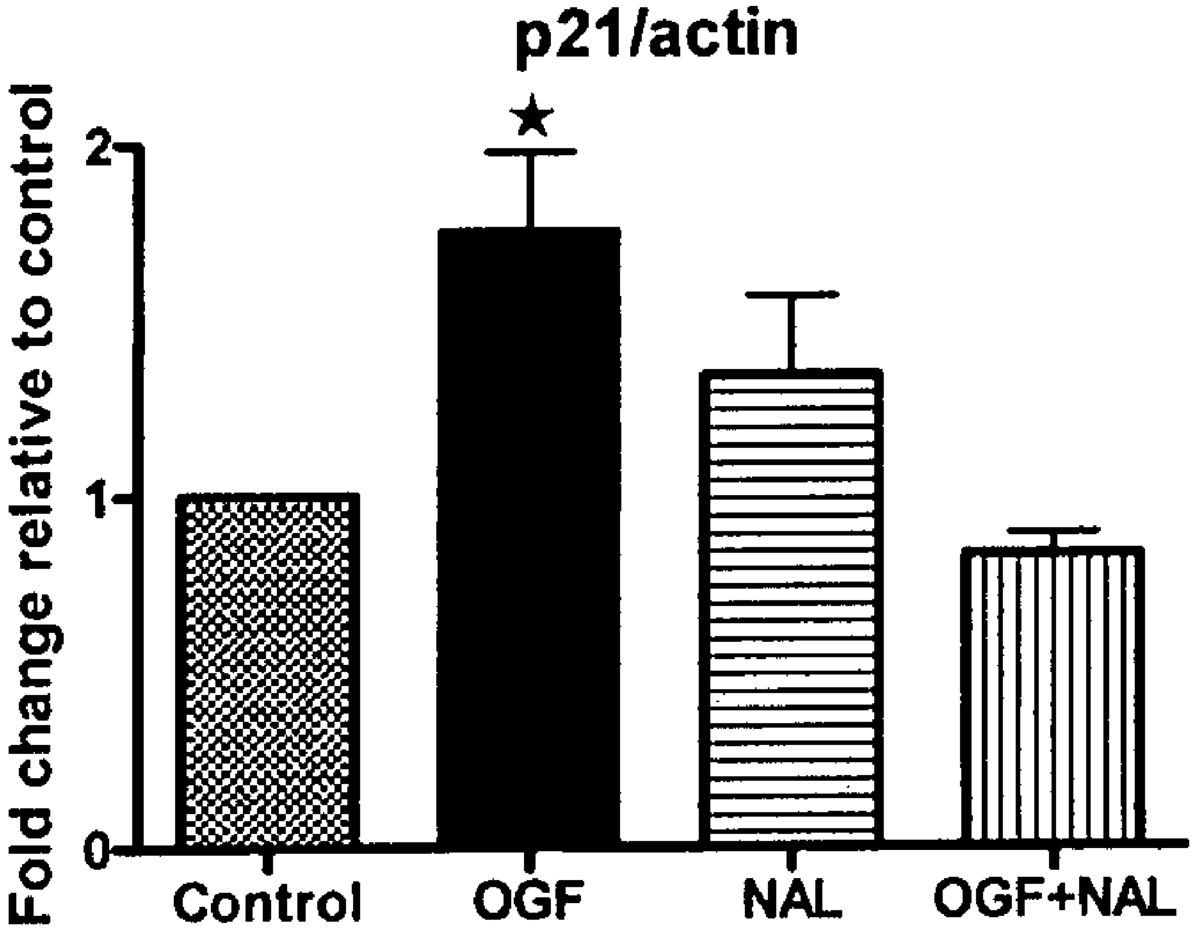
FIG. 7. Opioid receptor mediation of OGF action was evaluated in synchronized BxPC-3 cells treated with $10^{-6}$ M OGF, $10^{-5}$ M naloxone (NAL), both OGF and NAL, or sterile water (Control) for 9 hours. Protein lysates were resolved on SDS-PAGE, and subjected to Western blot analysis for p21 and actin. Densitometric analysis of p21 expression showed that p21 levels of OGF-treated cells were significantly elevated from controls at *$p<0.05$; no change was recorded in the NAL and OGF-NAL groups. Data represent means±SE for 3 independent experiments.

To demonstrate the opioid-receptor mediation of OGF, cells were treated concomitantly with the opioid antagonist naloxone and OGF. OGF-induced upregulation of p21 expression was blocked in cells exposed to both naloxone and OGF; naloxone alone had no effect on p21 expression (FIG. 7). This result showed that OGF-induced upregulation of p21 expression was receptor mediated. p21 is known as a tumor suppressor gene, functioning as a cell cycle inhibitor by forming heterotrimeric complexes with Cdks and cyclins. Therefore, the data suggest that under the effect of OGF, p21 protein levels were upregulated, and activated the p21-Rb pathway that, in turn, mediated the cell cycle blockade.

To investigate the role of other CKIs related to the p21-Rb pathway, p27 and p57 were assessed. Analysis of the expression of the cell cycle inhibitor p27 revealed that OGF treatment had no significant effect on expression levels of this CKI. p57 protein was not detected on Western blots (1:200 dilution) of BxPC-3 cells. Thus, only p21 is induced by OGF treatment in the pancreatic cancer cell lines studied.

Figure 8A:
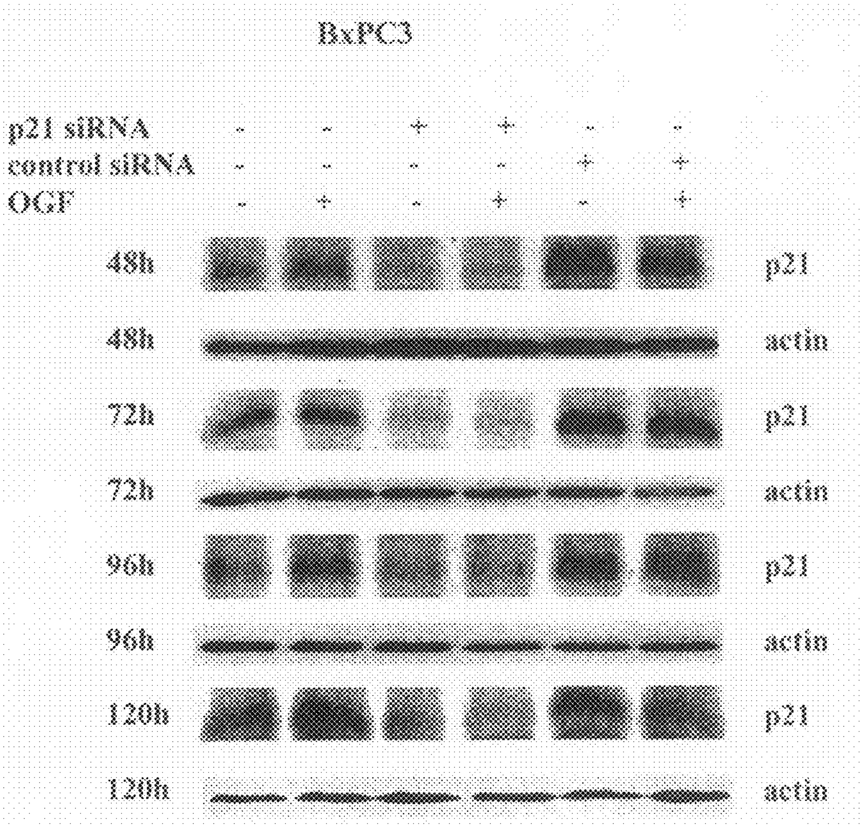
FIGS. 8A-8C. p21 is required for OGF-induced growth inhibition. BxPC-3 cells were transfected with p21 siRNAs or negative control siRNAs for 48, 72, 96, or 120 hours. Total proteins were isolated and separated by SDS-PAGE, and probed with antibodies specific to p21. Growth curves for BxPC-3 cells transfected with either p21 siRNA or negative control siRNA, and grown in the presence or absence of $10^{-6}$ M OGF for 96 or 120 hours. Cells were harvested at 48, 72, 96 or 120 hours, and counted with a hemacytometer. Data represent means±SE for 3 independent experiments. OGF had no effect on cell growth of cells transfected with p21 siRNA. Cell numbers for OGF-treated cultures transfected with negative control siRNA were significantly reduced from transfected cells receiving sterile water at *$p<0.05$ or ***$p<0.001$.
Figure 8B:
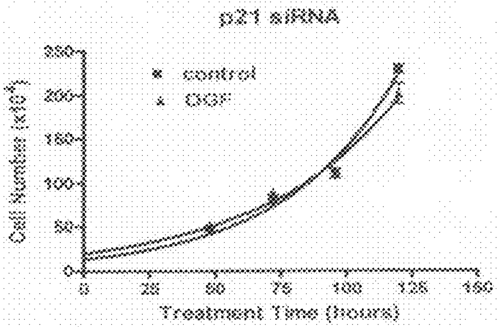
Figure 8C:
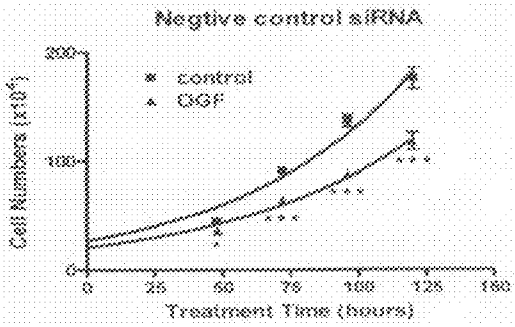

To validate the integral role of p21 in the OGF-induced inhibitory action on BxPC-3 cell growth, siRNA knockdown experiments were utilized. BxPC-3 cells were treated with p21 siRNA or with negative control siRNA. As revealed by Western blot analysis, the p21 siRNA markedly reduced the level of p21 protein at 48, 72, 96, and 120 hours in comparison to protein levels in cells transfected with control siRNA (FIG. 8A). Growth analysis of cells transfected with p21 siRNAs and subsequently exposed to OGF for 120 hours, showed that p21 induction is required for the OGF inhibitory action on BxPC-3 cells (FIG. 8B). BxPC-3 cells transfected with the negative control siRNAs and exposed to OGF exhibited significant reductions in growth of 17.8%, 28.6%, 35.8%, and 33.0% at 48, 72, 96, and 120 hours, respectively. See FIG. 8C.

To examine the ubiquity of the role of p21 as a cyclin-dependent kinase inhibitor, two other human pancreatic cancer cell lines were examined: PANC-1 and Capan-2. In synchronized PANC-1 cells, OGF increased p21 expression at 6 hours relative to levels in control cells. Western blot analysis of protein isolated from these cells transfected with p21 siRNA revealed a 51% reduction in p21 levels in comparison to control cells at 96 hours. Growth curves indicated that OGF had no inhibitory effect on PANC-1 cells lacking p21, but OGF exposure markedly decreased growth by 34.1% at 72 hours and 35.5% at 96 hours in cells transfected with the negative control siRNAs compared to transfected cultures treated with sterile water. In Capan-2 cells, OGF increased p21 expression at 3 hours relative to control cultures. Capan-2 cells transfected with p21 siRNA had 60% of p21 levels at 72 hours relative to cells transfected with control siRNA. Growth curves revealed that OGF had no inhibitory action on Capan-2 cells lacking p21, but OGF did depress growth of Capan-2 cells transfected with negative control siRNA at 48, 72, and 96 hours.

Example 4

OGF Modulation of Normal Cells

OGFr is required for OGF action on growth. Normal Human Neo-Epidermal Keratinocyte cells (NHEK) were transfected with OGFr siRNAs or control siRNAs for 72 h in the presence of $10^{-6}$ M OGF, $10^{-6}$ M NTX, or sterile water. Cells were harvested at 72 h and counted with a hemacytometer. Data represent means±SE for 2 independent experiments. Cell numbers differed from wt cells or cells transfected with the negative control siRNA and treated with sterile water at p<0.05 (*), p<0.01 (), or p<0.01 (*). See FIG. 9. NHEK cells seeded into 6-wells plates and treated with $10^{-6}$ M OGF for 96 hr and counted daily revealed significant reductions (p<0.01 at 72 hr and p<0.001 at 96 hr) in cell numbers in OGF-treated cultures relative to controls. At 72 hr, OGF-treated cultures had 20% fewer cells and at 96 hr, OGF-treated cultures had 32% fewer cells than sterile-water treated control cultures. Analysis of growth curve data revealed doubling times of 37.4 hr for control NHEK cells and 57.1 hr for OGF-exposed NHEK cells.

Another normal cell line, human umbilical vein endothelial cells (HUVEC) has been subjected to OGF exposure. Cell number after 48, 72, and 96 hr of treatment with $10^{-6}$M OGF resulted in significant (p<0.01) reductions in cell number in OGF cultures relative to sterile-water treated control HUVEC cultures. At 96 hr, OGF-treated cultures had 45.9% fewer cells than normal cultures.

Example 5

OGF Treatment of Rabbit Tenon's Fibroblasts in Glaucoma

OGF in dosages ranging from 10–4 to $10^{-7}$ M were added to 24-well cultures for 72 hours; sterile water served as control. Drug or vehicle, and media were changed daily. Cell counts of Rabbit Tenon's Fibroblast cells (RTCFs) treated with OGF ($10^{-7}$ to $10^{-5}$ M) were 28%, 33%, and 37% smaller than controls (p<0.001). RTCFs treated with $10^{-4}$ M OGF showed a decrease in proliferation of 47% compared to controls (p<0.001), as well as a 26% (p<0.01) and 22% (p<0.05) decrease in cell proliferation compared to RTCFs treated with $10^{-7}$ to $10^{-6}$ M OGF.

What is claimed is:

1. A method for monitoring the sensitivity of opioid growth factor (OGF) modulation or treatment of a cell proliferation or growth related condition in a subject, comprising assessing the level of a cyclin dependent kinase inhibitor (CKI) or the level of a CKI/cyclin dependent kinase (CDK) complex in the subject, and determining the sensitivity of the OGF modulation or treatment based on the level of said CKI or the level of said CKI/CDK complex.

2. The method of claim 1, wherein the modulation or treatment of the condition results in an increased cell growth or proliferation comprising decreasing, disrupting or inhibiting OGF receptor (OGFr) expression in the cell to be modulated or treated.

3. A method for screening the eligibility of a subject for opioid growth factor (OGF) modulation or treatment of a cell proliferation or growth related condition, comprising assessing the level of OGF receptor (OGFr) and a cyclin dependent kinase inhibitor (CKI) relevant or corresponding to the condition in the cell to be modulated or treated, wherein the cell having at least one molecule of OGFr and one molecule of the CKI indicates the subject's eligibility.

4. A method for enhancing the efficacy of opioid growth factor (OGF) modulation or treatment of a cell growth or proliferation related disorder in a subject, comprising administering a compound to increase the level of a cyclin dependent kinase inhibitor (CKI) in the cell to be modulated or treated, and administering to the subject an effective amount of OGF to the subject.

5. The method of claim 4 further comprising, prior to the administration of OGF, enhancing the expression of the OGF receptor (OGFr) in the cells to be modulated or treated.

6. A method for enhancing the efficacy of opioid growth factor (OGF) modulation or treatment of a cell growth or proliferation related disorder in a subject, comprising enhancing the expression of the OGF receptor (OGFr) in the cells to be modulated or treated, and administering to the subject an effective amount of OGF.

7. The method of claim 6 further comprising, prior to the administration of OGF, administering a compound to increase the level of the cyclin dependent kinase inhibitor (CKI) relevant or corresponding to the disorder in the cells to be modulated or treated.

8. The method of claim 1, further comprising assessing the level of retinoblastoma (Rb) protein phosphorylation in the subject.

9. The method of any one of claims 1, 3-4 and 6, wherein the cell is a human cell.

10. The method of any one of claims 1, 3-4 and 6, wherein the OGF is administered to the subject at a dose of from about 20 to about 1000 μg/kg body weight.

11. The method of claim 10, wherein the OGF is administered to the subject at a dose of from about 100 to about 400 μg/kg body weight.

12. The method of any one of claims 1, 3-4 and 6, wherein the cell is a neoplastic cell derived from or characterized as being a pancreatic cancer, squamous cell carcinoma, breast cancer, colorectal cancer, renal cancer, brain cancer, prostate cancer, bladder cancer, bone cancer, joint cancer, uterine cancer, cervical cancer, endometrial cancer, multiple myeloma, Hodgkin's disease, non-Hodgkin's lymphoma, melanoma, leukemias, lung cancer, ovarian cancer, gastrointestinal cancer, Kaposi's sarcoma, liver cancer, pharyngeal cancer or laryngeal cancer.

13. The method of claim 1, wherein the assessing the CKI comprises detecting the subject's CKI expression level before OGF administration, administering an effective amount of OGF to the subject, detecting the subject's CKI expression level after the administration of OGF, and compare the subject's CKI expression levels before and after the administration of OGF, wherein the CKI expression results in at least one CKI molecule increase after the administration of OGF indicates that the subject is sensitive to OGF therapy.

14. The method of claim 13, wherein the CKI expression is detected by standard methods selected from the group consisting of ELISA, radioimmunoassay, Western blotting techniques, PCR, Northern blotting, and Southern blotting.

15. The method of claim 13, wherein the CKI is p16 or p21.

16. The method of claim 15, wherein at least one p21 molecule increase after the administration of OGF indicates sensitivity to OGF therapy for pancreatic adenocarcinoma.

17. The method of claim 15, wherein at least one p16 molecule increase after the administration of OGF indicates sensitivity to OGF therapy for squamous cell carcinoma.

18. The method of any one of claims 1, 3-4 and 6, wherein the CDK inhibitor is selected from the group consisting of p15, p16, p18, p19, p21, p27 and p57.

19. The method of claim 4, wherein said cell expresses OGFr.

* * * * *

UNITED STATES PATENT AND TRADEMARK OFFICE

CERTIFICATE OF CORRECTION

PATENT NO. : 7,807,368 B2
APPLICATION NO. : 11/901770
DATED : October 5, 2010
INVENTOR(S) : Zagon et al.

It is certified that error appears in the above-identified patent and that said Letters Patent is hereby corrected as shown below:

On the title page item (54) and Col. 1, line 1, should read:

CYCLIN-DEPENDENT KINASE INHIBITORS AS TARGETS FOR OPIOID GROWTH FACTOR TREATMENT

Signed and Sealed this
Twenty-eighth Day of December, 2010

David J. Kappos
*Director of the United States Patent and Trademark Office*

SEQUENCE LISTING

```
<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: synthetic primer

<400> SEQUENCE: 1

gtagaattcc cgccgagcat ggacgacccc gact                              34


<210> SEQ ID NO 2
<211> LENGTH: 36
<212> TYPE: DNA
<213> ORGANISM: Artificial Sequence
<220> FEATURE:
<223> OTHER INFORMATION: synthetic primer

<400> SEQUENCE: 2

ttatctagat tattaaggct tcccagactt ggcaga                            36


<210> SEQ ID NO 3
<211> LENGTH: 19
<212> TYPE: RNA
<213> ORGANISM: Artificial Sequence
<220> FEATURE:
```

-continued

```
<223> OTHER INFORMATION: synthetic small RNA molecule

<400> SEQUENCE: 3

uagaaacuca gguuuggcg                                           19


<210> SEQ ID NO 4
<211> LENGTH: 19
<212> TYPE: RNA
<213> ORGANISM: Artificial Sequence
<220> FEATURE:
<223> OTHER INFORMATION: synthetic small RNA molecule

<400> SEQUENCE: 4

cgccaaaccu gaguuucua                                           19


<210> SEQ ID NO 5
<211> LENGTH: 21
<212> TYPE: RNA
<213> ORGANISM: Artificial Sequence
<220> FEATURE:
<223> OTHER INFORMATION: synthetic small RNA molecule

<400> SEQUENCE: 5

acaccgcuuc ugccuuuucu u                                        21


<210> SEQ ID NO 6
<211> LENGTH: 21
<212> TYPE: RNA
<213> ORGANISM: Artificial Sequence
<220> FEATURE:
<223> OTHER INFORMATION: synthetic small RNA molecule

<400> SEQUENCE: 6

gaaaaggcag aagcgguguu u                                        21
```